United States Patent
Vandenbossche et al.

(10) Patent No.: US 6,605,124 B1
(45) Date of Patent: Aug. 12, 2003

(54) CATIONIC COUPLERS AND THEIR USE FOR OXIDATION DYEING

(75) Inventors: Jean-Jacques Vandenbossche, Tartas (FR); Laurent Vidal, Paris (FR); Jean-Baptiste Saunier, Paris (FR); Alain LaGrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/646,647

(22) PCT Filed: Jan. 21, 2000

(86) PCT No.: PCT/FR00/00140
§ 371 (c)(1),
(2), (4) Date: Nov. 22, 2000

(87) PCT Pub. No.: WO00/43356
PCT Pub. Date: Jul. 27, 2000

(30) Foreign Application Priority Data

Jan. 21, 1999 (FR) .............................. 99 00639

(51) Int. Cl.$^7$ ................................ A61K 7/13
(52) U.S. Cl. .............. 8/405; 8/406; 8/409; 8/410; 8/421; 8/424; 430/378; 430/547; 430/566; 430/567
(58) Field of Search ................. 8/408, 421, 424, 8/405, 406, 409, 410; 430/566, 547, 567, 378

(56) References Cited

U.S. PATENT DOCUMENTS

| | | | |
|---|---|---|---|
| 4,003,699 A | | 1/1977 | Rose et al. ............ 8/10.2 |
| 4,269,928 A | * | 5/1981 | Mason et al. ............ 430/239 |
| 4,823,985 A | | 4/1989 | Grollier et al. ............ 222/1 |
| 5,061,289 A | | 10/1991 | Clausen et al. ............ 8/405 |
| 5,210,012 A | * | 5/1993 | Ono et al. ............ 430/566 |
| 5,344,463 A | | 9/1994 | Chan et al. ............ 8/408 |
| 5,380,340 A | | 1/1995 | Neunhoeffer et al. ............ 8/409 |
| 5,672,180 A | | 9/1997 | Lim et al. ............ 8/408 |
| 5,766,576 A | | 6/1998 | Löwe et al. ............ 424/62 |
| 5,849,042 A | | 12/1998 | Lim et al. ............ 8/408 |

FOREIGN PATENT DOCUMENTS

| | | | |
|---|---|---|---|
| DE | 23 59 399 | | 6/1975 |
| DE | 38 43 892 | | 6/1990 |
| DE | 285 095 | | 12/1990 |
| DE | 41 33 957 | | 4/1993 |
| DE | 195 43 988 | | 5/1997 |
| EP | 0303301 | * | 2/1989 |
| EP | 0 345 728 | | 12/1989 |
| FR | 2 586 913 | | 3/1987 |
| FR | 2 733 749 | | 11/1996 |
| FR | 2 750 048 | | 12/1997 |
| GB | 1 026 978 | | 4/1966 |
| GB | 1 153 196 | | 5/1969 |
| GB | 2016502 | * | 2/1978 |
| GB | 1 563 674 | | 3/1980 |
| JP | 63-258843 | | 10/1988 |
| JP | 1-186859 | | 7/1989 |
| JP | 2-19576 | | 1/1990 |
| JP | 02244041 | * | 9/1990 |
| JP | 8-310999 | | 11/1996 |
| JP | 9-110659 | | 4/1997 |
| WO | WO 94/08969 | | 4/1994 |
| WO | WO 94/08970 | | 4/1994 |
| WO | WO 96/15765 | | 5/1996 |

OTHER PUBLICATIONS

Search Report related to the Hirano et al. "Silver halide photographic materials", ACS. Document No. CA. 115:60731, 1991.*
Patent Abstracts of Japan, vol. 014, No. 565, Dec. 17, 1990, JP 02 244041.
English language Derwent Abstract of DD 285 095, Dec. 1990.
English language Derwent Abstract of FR 2 733 749, Nov. 1996.
English language Derwent Abstract of FR 2 750 048, Dec. 1997.
English language Derwent Abstract of JP 63–258843, Oct. 1988.
English language Derwent Abstract of JP 1–186859, Jul. 1989.
English language Derwent Abstract of JP 2–19576, Jan. 1990.
English language Derwent Abstract of JP 8–310999, Nov. 1996.
English language Derwent Abstract of JP 9–110659, Nov. 1997.

* cited by examiner

*Primary Examiner*—Gregory Delcotto
*Assistant Examiner*—Eisa Elhilo
(74) *Attorney, Agent, or Firm*—Finnegan, Henderson, Farabow, Garrett & Dunner, L.L.P.

(57) ABSTRACT

The subject of the invention is novel compounds derived from naphth-1-ol comprising at least one cationic group, their use as coupler for the oxidation dyeing of keratinous fibres, compositions for the oxidation dyeing of keratinous fibres, and in particular human keratinous fibres such as hair, containing them in combination with at least one oxidation base, as well as methods of oxidation dyeing using them.

36 Claims, No Drawings

CATIONIC COUPLERS AND THEIR USE FOR OXIDATION DYEING

The invention relates to novel compounds derived from naphth-1-ol which can be represented by formula (I) and comprising at least one cationic group Z of formula (II), their use as coupler for the oxidation dyeing of keratinous fibres, compositions for the oxidation dyeing of keratinous fibres, and in particular human keratinous fibres such as hair, containing them in combination with at least one oxidation base, as well as the oxidation dyeing methods using them.

It is known to dye keratinous fibres and in particular human hair with dyeing compositions containing oxidation dye precursors, in particular para-phenylenediamines, ortho- or para-aminophenols, heterocyclic compounds such as diaminopyrazole derivatives, generally called oxidation bases. Oxidation dye precursors, or oxidation bases, are colourless or weakly coloured compounds which, combined with oxidizing products, can give rise, through a process of oxidative condensation, to coloured or colouring compounds.

It is also known that it is possible to vary the shades obtained with these oxidation bases by combining them with couplers or colour modifiers, the latter being chosen in particular from aromatic meta-diamines, meta-aminophenols, meta-diphenols, noncationic naphthols or alternatively certain heterocyclic compounds such as for example indolic couplers.

The variety of molecules used in oxidation bases and couplers allows a rich palette of colours to be obtained.

The so-called "permanent" colour obtained using these oxidation dyes must moreover satisfy a number of requirements. Thus, it must be without drawbacks from the toxicological point of view, it must make it possible to obtain shades in the desired intensity and exhibit good resistance towards external agents (light, adverse weather conditions, washing, permanent waving, perspiration, rubbing).

The dyes must also make it possible to cover grey hair and must finally be the least selective possible, that is to say make it possible to obtain the smallest possible differences in colour right along the same keratinous fibre, which may indeed be differently sensitized (i.e. damaged) between its tip and its root.

However, the applicant has now just discovered, completely unexpectedly and surprisingly, that the use, as coupler, of novel compounds of the 2-acylaminonaphth-1-ol, 2-amidonaphth-1-ol and 2-sulphonylaminonaphth-1-ol type, comprising at least one cationic group Z of formula (II) as defined below, and which can be represented by formula (I) as defined below, makes it possible to obtain dyeing compositions leading to intense colours, in shades ranging from red to blue and exhibiting, furthermore, remarkable fastness to light, adverse weather conditions, washing, perspiration or permanent waving.

These discoveries form the basis of the present invention.

The first subject of the invention is therefore a compound of the following formula (I), as well as its addition salts with an acid:

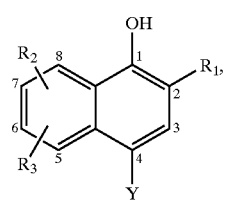

(I)

in which:

$R_1$ represents a group chosen from $-NR_4(C=O)R_5$, $-NR_6SO_2R_7$ and $-(C=O)NR_6R_8$, the radicals $R_4$, $R_5$, $R_6$, $R_7$ and $R_8$ being as defined below;

$R_2$ and $R_3$, which are identical or different, represent a hydrogen atom; a halogen atom; a group Z as defined below; a radical comprising from 1 to 20 carbon atoms, linear or branched (it being possible for the branch(es) to form one or more carbon-containing rings comprising from 3 to 7 members), which may contain one or more double bonds and/or one or more triple bonds (the said double bonds possibly leading to aromatic groups), in which one or more carbon atoms may be replaced with an oxygen, nitrogen or sulphur atom or with an $SO_2$ group, and in which the carbon atoms may, independently of each other, be substituted with one or more halogen atoms;

it being understood that:

the said radicals $R_2$ and $R_3$ cannot be linked to the benzene ring of formula (I) by an —NH—NH— bond; and that $R_2$ and $R_3$ do not contain a peroxide bond or diazo, nitro and nitroso radicals;

that $R_2$ and $R_3$ cannot represent a hydroxyl radical or a thio radical;

that $R_2$ and $R_3$ cannot represent, simultaneously, an amino, alkylamino, acylamino or sulphonylamino radical;

Y represents a hydrogen or halogen atom; a group $-OR_9$, $-SR_9$, or $-NH-SO_2R_9$ in which $R_9$ represents a $C_1-C_6$ alkyl radical, linear or branched (it being possible for the branch(es) to then form one or more rings comprising from 3 to 6 members), unsubstituted or substituted with one or more radicals chosen from the group consisting of a halogen atom, a hydroxyl, $C_1-C_4$ alkoxy, amino and amino($C_1-C_4$ alkyl) radical; a phenyl radical, unsubstituted or substituted with one or two radicals chosen from the group consisting of a $C_1-C_4$ alkyl, trifluoromethyl, carboxyl, $C_1-C_4$ alkoxycarbonyl, halogen, hydroxyl, $C_1-C_4$ alkoxy, amino and amino($C_1-C_4$ alkyl) radical; or a benzyl radical;

$R_4$, $R_6$ and $R_8$, which are identical or different, represent a hydrogen atom; a group Z as defined below; a radical comprising from 1 to 15 carbon atoms, linear or branched (it being possible for the branch(es) to form one or more carbon-containing rings comprising from 3 to 7 members), which may contain one or more double bonds and/or one or more triple bonds (the said double bonds possibly leading to aromatic groups), in which one or more carbon atoms may be replaced with an oxygen, nitrogen or sulphur atom or with an $SO_2$ group, and in which the carbon atoms may, independently of each other, be substituted with one or more halogen atoms;

it being understood that the said $SO_2$ group is not directly linked to the nitrogen atom carrying the radical $R_4$ or $R_6$;

it being understood that the group $-(C=O)-$ is not directly linked to the nitrogen atom carrying the radical $R_6$;

it being understood that the said radicals $R_4$, $R_6$ and $R_8$ do not contain a peroxide bond or diazo, nitro and nitroso radicals;

it being understood that the radicals $R_4$, $R_6$ and $R_8$ cannot represent a hydroxyl radical, a thio radical, an amino radical, an alkoxy radical, an alkylthio radical;

$R_5$ and $R_7$, which are identical or different, represent a hydrogen atom; a group Z as defined below; a radical comprising from 1 to 20 carbon atoms, linear or branched (it being possible for the branch(es) to form one or more carbon-containing rings comprising from 3 to 7 members), which may contain one or more double bonds and/or one or more triple bonds (the said double bonds possibly leading to aromatic groups), in which one or more carbon atoms may be replaced with an oxygen, nitrogen or sulphur atom or with an $SO_2$ group, and in which the carbon atoms may, independently of each other, be substituted with one or more halogen atoms;

it being understood that the said radicals $R_5$ and $R_7$ do not contain peroxide bonds or diazo, nitro and nitroso radicals;

it being understood that $R_5$ cannot represent a hydroxyl radical or a thio radical;

it being understood that $R_7$ cannot represent a thio radical;

it, being understood that the radicals $R_4$ and $R_5$ on the one hand, and the radicals $R_6$ and $R_8$ on the other hand, can, in addition, be linked to form, independently of each other, a saturated or unsaturated ring comprising from 5 to 7 members, consisting of carbon, nitrogen and/or acyl, each member being unsubstituted or substituted with 1 or 2 radicals R, which are identical or different, R being a $C_1-C_8$ alkyl radical, linear or branched (it being possible for the branch(es) to then form one or more rings comprising from 3 to 7 members), which may contain one or more double bonds and/or one or more triple bonds (the said double bonds possibly leading to aromatic groups), and in which one or more carbon atoms may be replaced with an oxygen, nitrogen or sulphur atom or with an $SO_2$ group, and in which the carbon atoms may, independently of each other, be substituted with one or more halogen atoms; the said ring containing no peroxide bonds or diazo, nitro and nitroso radicals;

Z is a cationic group represented by the following formula (II):

in which:

n can take the value 0 or 1;

B represents an alkyl radical comprising from 1 to 15 carbon atoms, linear or branched (it being possible for the branch(es) to then form one or more rings comprising from 3 to 7 members), which may contain one or more double bonds and/or one or more triple bonds, the said double bonds possibly leading to aromatic groups, and in which one or more carbon atoms may be replaced with an oxygen, nitrogen or sulphur atom or with an $-SO_2$ radical; and in which one or more carbon atoms may, independently of each other, be substituted with one or more halogen atoms or with one or more groups Z; the said radical B containing no peroxide bond or diazo, nitro or nitroso radicals;

D is chosen from the cationic groups of the following formulae (III) and (IV):

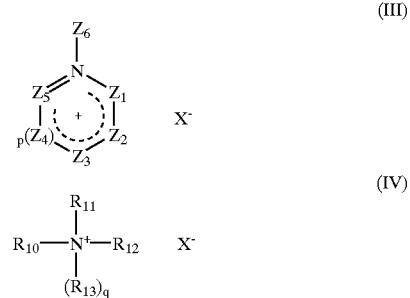

in which:

p and q can, independently of each other, take the value 0 or 1;

the radical B is linked to the group D by any one of the atoms of the radical D;

when n=0 and q=0, then the group of formula (IV) can be linked to the compound of formula (I) directly by the nitrogen atom of the quaternary ammonium;

$Z_1$, $Z_2$, $Z_3$ and $Z_4$, independently of each other, represent an oxygen atom; a sulphur atom; a nitrogen atom which is unsubstituted or substituted with a radical $R_{14}$; a carbon atom which is unsubstituted or substituted with one or two radicals $R_{14}$, which are identical or different;

$Z_5$ represents a nitrogen atom or a carbon atom which is unsubstituted or substituted with a radical $R_{14}$;

$Z_6$ can have the same meanings as those indicated below for the radical $R_{14}$; it being understood that $Z_6$ is different from a hydrogen atom;

the radicals $Z_1$ or $Z_5$ can, in addition, form with $Z_6$ a saturated or unsaturated ring comprising from 5 to 7 members, each member being unsubstituted or substituted with one or two radicals $R_{14}$ which are identical or different;

$R_{14}$ represents a hydrogen atom; a group Z; a radical comprising from 1 to 10 carbon atoms, linear or branched, which may contain one or more double bonds and/or one or more triple bonds, it being possible for the said double bonds to then possibly lead to aromatic groups, and in which one or more carbon atoms may be replaced with an oxygen, nitrogen or sulphur atom, or with an $SO_2$ group, and in which one or more carbon atoms may, independently of each other, be substituted with one or more halogen atoms; the said radical containing no peroxide bond or diazo, nitro and nitroso radicals;

it being possible, in addition, for two of the adjacent radicals $Z_1$, $Z_2$, $Z_3$, $Z_4$ and $Z_5$ to form a ring comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;

$R_{10}$, $R_{11}$, $R_{12}$ and $R_{13}$, which are identical or different, have the same meanings as those indicated above for the radical $R_{14}$;

it being possible for the radicals $R_{10}$, $R_{11}$, $R_{12}$ and $R_{13}$ to also form, in pairs with the quaternary nitrogen atom to which they are attached, one or more saturated rings comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;

$X^-$ represents an organic or inorganic anion and is preferably chosen from the group consisting of a halide group such as chloride, bromide, fluoride, iodide; a hydroxide; a sulphate; a hydrogen sulphate; a ($C_1$–$C_6$)alkyl sulphate such as for example a methyl sulphate or an ethyl sulphate; an acetate; a tartrate; an oxalate; a ($C_1$–$C_6$)alkyl sulphonate such as for example a methyl sulphonate; an aryl sulphonate which is unsubstituted or substituted with a $C_1$–$C_4$ alkyl radical such as for example a toluoyl sulphonate;

it being understood that at least one of the groups $R_1$ to $R_3$ represents or contains a group Z.

According to the invention, when it is indicated that one or more of the carbon atoms of the radical(s) $R_1$ to $R_8$ can be replaced with an oxygen, nitrogen or sulphur atom or with an $SO_2$ group, and/or that the said radicals $R_1$ to $R_8$ may contain one or more, double bonds and/or one or more triple bonds, that means that it is possible, by way of example, to make the following conversions:

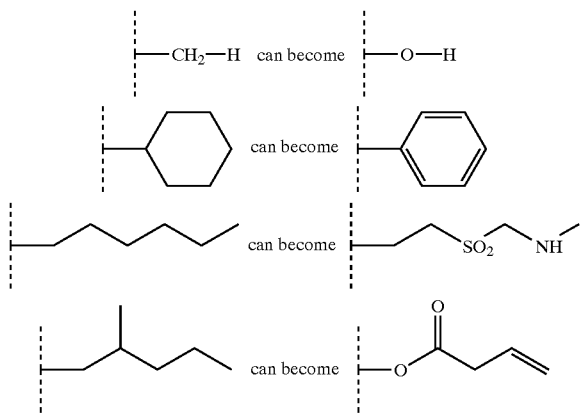

According to the invention, $R_2$ and $R_3$ preferably represent, independently of each other, a hydrogen or chlorine atom; a group Z; a methyl or methoxy radical; an amino, methylamino, 2-hydroxyethylamino radical; a group —NH(CO)$R_{15}$ in which $R_{15}$ represents one of the radicals listed in the group (G1) consisting of a methyl, ethyl, propyl, isopropyl, butyl, isobutyl, tert-butyl, pentyl, isopentyl, neopentyl, hexyl, cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, pyridinyl, chloropyridinyl, dichloropyridinyl, 5-(bromo)pyridin-3-yl, piperazin-2-yl, 2-chloro-4-(trifluoromethyl)pyperimidin-5-yl, quinoxal-2-yl, benzofurazan-5-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, (methoxycarbonyl)methyl, 2-carboxyethyl, 2-(methoxycarbonyl)ethyl, 2-carboxycyclopropyl, 2-carboxycyclohexane, methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl radical; or a group —NHSO$_2$R$_{16}$ in which R$_{16}$ represents one of the radicals listed in the group (G2) consisting of the methyl, trifluoromethyl, ethyl, 2-chloroethyl, propyl, 3-chloropropyl, isopropyl, butyl, thiophen-2-yl, hydroxyl, ethoxy, amino and dimethylamino radicals.

Among these radicals, there are more particularly preferred for $R_2$ and $R_3$, independently of each other, a hydrogen atom; a group —O—E—D', —NH—E—D', —NH(CO)—D', —NH(CO)—E—D', —NH(CO)O—E—D', —NH(CO)NH—E—D' or —NH(SO$_2$)—E—D', in which —E— represents a —(CH$_2$)$_q$— arm, q being an integer equal to 1 or 2, and in which D' represents the 3-methylimidazolidinium-1-yl, 3-(2-hydroxyethyl) imidazolidinium-1-yl, 1,2,4-triazolinium-1-yl, 1,2,4-triazolinium-4-yl, N—(C$_1$–C$_4$)alkylpyridinium-2-yl, N—(C$_1$–C$_4$)alkylpyridinium-3-yl, N—(C$_1$–C$_4$)alkylpyridinium-4-yl, N-(2-hydroxyethyl)pyridinium-2-yl, N-(2-hydroxyethyl)pyridinium-3-yl, N-(2-hydroxyethyl)pyridinium-4-yl, pyridinium-1-yl, tri(C$_1$–C$_4$ alkyl)ammonium-N-yl, 1-methylpiperidinium-1-yl and 1,4-dimethylpiperazinium-1-yl groups; a methyl, methoxy, amino or methylamino radical; or a group —NH(CO)R$_{17}$ in which R$_{17}$ represents one of the radicals listed in the group (G2) as defined above; or a methanesulphonylamino, ethanesulphonylamino or dimethylaminosulphonylamino group.

According to the invention, $R_4$ preferably represents a hydrogen atom or a group A$_1$, A$_2$, A$_3$, A$_4$ or A$_5$, optionally separated from the nitrogen of the group —NR$_4$(C═O)R$_5$ by a group —(CO)—.

"Group A$_1$" is understood to mean a linear or branched C$_1$–C$_8$ alkyl radical which may carry one or two double bonds or one triple bond, which may be unsubstituted or substituted with a group chosen from a group A$_2$, a group A$_4$, a group A$_5$, which may be unsubstituted or substituted with one or two groups, which are identical or different, chosen from the N—(C$_1$–C$_3$)alkylamino, N—(C$_1$–C$_3$)alkyl-N—

($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano and carboxyl groups, and which may be unsubstituted or substituted with one or more hydroxyl, fluoro or chloro groups.

"Group $A_2$" is understood to mean an aromatic group of the phenyl or naphthyl type, which may be unsubstituted or substituted with one to three groups, which are identical or different, chosen from the methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups.

"Group $A_3$" is understood to mean heteroaromatic groups chosen from the furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl groups, the said heteroaromatic groups being unsubstituted or substituted with 1 to 3 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical.

"Group $A_4$" is understood to mean a $C_3$–$C_7$ cycloalkyl radical, a norbonyl radical, carrying or otherwise a double bond and unsubstituted or substituted with 1 or 2 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical.

"Group $A_5$" is understood to mean a heterocycle chosen from the dihydrofuranyl, tetrahydrofuranyl, butyrolactonyl, dihydrothiophenyl, tetrahydrothiophenyl, tetrahydrothiophenonyl, iminothiolane, dihydropyrrolyl, pyrrolidinyl, pyrrolidinonyl, imidazolidinonyl, imidazolidinethionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridinyl, piperidinyl, pentalactam, morpholinyl, pyrazoli(di)nyl, pyrimi(di)nyl, pyrazinyl, piperazinyl and azepinyl rings.

Among these radicals, $R_4$ represents more particularly a hydrogen atom; a methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; or a 2-hydroxyethyl, 2-methoxyethyl or 2-ethoxyethyl group.

Still more preferably, $R_4$ represents a hydrogen atom or a methyl radical.

According to the invention, $R_5$ preferably denotes a hydrogen atom, an amino group; a group Z; a group $A_1$, $A_2$, $A_3$, $A_4$ or $A_5$ as defined above, optionally separated from the carbon (at the 2-position) with respect to the amide function of the compound of formula (I) by a group —O—, —NH, —N($C_1$–$C_3$)alkyl- or —(CO)—.

Among these radicals, a group Z or a radical chosen from the group (G1) as defined above is more particularly preferred for $R_5$.

Still more preferably, $R_5$ represents a group Z; a radical chosen from the group (G3) consisting of a methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl or 4-morpholinyl radical.

Still more preferably, $R_5$ represents a group —D', —E—D', —O—E—D' or —NH—E—D' in which —E— represents a —($CH_2$)$_q$— arm, q being an integer equal to 1 or 2 and D' a group as defined above; or a radical chosen from the group (G4) consisting of a methyl, methoxymethyl, 2-carboxyethyl, methoxy, amino, ethylamino and 1-pyrrolidinyl radical.

When $R_4$ and $R_5$ form a ring, the said ring is preferably chosen from the 2-pyrrolidinon-1-yl, methyl-2-pyrrolidinon-1-yl, 5-carboxy-2-pyrrolidinon-1-yl, 5-methoxycarbonyl-2-pyrrolidinon-1-yl, pyrazolinon-1-yl, succinimid-1-yl, 3,5-diketopyrazolidin-1-yl, oxindolin-1-yl, maleimid-1-yl, isoindole-1,3-dion-2-yl, 2-piperidinon-1-yl and glutarimid-1-yl groups.

According to the invention, $R_6$ preferably represents a hydrogen atom or a group $A_1$, $A_2$, $A_3$, $A_4$ or $A_5$ as defined above.

There is more particularly preferred for $R_6$ a hydrogen atom; a methyl, ethyl, isopropyl, allyl; phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; a 2-hydroxyethyl, 2-methoxyethyl or 2-ethoxyethyl group.

Still more particularly, $R_6$ represents a hydrogen atom or a methyl radical.

According to the invention, $R_8$ preferably denotes a group Z; a hydrogen atom or a group $A_1$, $A_2$, $A_3$, $A_4$ or $A_5$ as defined above.

There is more particularly preferred for $R_8$ a group Z; a hydrogen atom; a methyl, ethyl, isopropyl, allyl; phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; a 2-hydroxyethyl, 2-methoxyethyl or 2-ethoxyethyl group.

Still more preferably, $R_8$ represents a hydrogen atom or a methyl radical, a group —D', —E—D', in which —E— represents a —($CH_2$)$_q$— arm, q being an integer equal to 1 or 2, and D' a group as defined above.

When $R_6$ and $R_8$ form a ring, the said ring is preferably chosen from the pyrrolidinyl, piperidinyl, morpholinyl, pyrazolyl, isoxazolyl, imidazolyl, thiazolyl, indolyl, indolidinyl, indazolyl, pyrazolotriazolyl, pyrrolotriazolyl, pyrazoloimidazolyl, pyrazolidinyl, thiomorpholinyl, thiazolyl and pyrazinyl groups.

According to the invention, $R_7$ preferably denotes an amino group; a group Z; a group $A_1$, a group $A_2$, a group $A_3$, a group $A_4$ or a group $A_5$ as defined above, optionally separated from the sulphur of the sulphonyl group of the compound of formula (I) by a group —NH or N($C_1$–$C_3$) alkyl-.

Among these radicals, there are more particularly preferred for $R_7$ a group Z, one of the radicals listed in the group (G4) consisting of methyl, trifluoromethyl, ethyl, 2-chloroethyl, propyl, 3-chloropropyl, isopropyl, butyl, thiophen-2-yl, hydroxyl, ethoxy, amino and dimethylamino radicals.

Still more preferably, $R_7$ represents a group —D', —E—D' or —NH—E—D', in which —E— represents a —$(CH_2)_q$— arm, q being an integer equal to 1 or 2, and D' a group as defined above; a methyl, ethyl or dimethylamino radical.

According to the invention, Y preferably represents a radical chosen from the group comprising: a hydrogen, chlorine, fluorine or bromine atom; the methoxy, ethoxy, propoxy, benzyloxy and phenoxy groups; —$OCH_2CH_2OMe$; —$OCH_2CH_2OMe$; —$OCH_2CH_2NMe_2$; —$OCH_2(CO)OH$, —$OCH_2(CO)OMe$, —$OCH_2(CO)Oet$, —$SCH_2CH_2CO_2H$ and $NHSO_2Me$ groups.

Among these radicals, there are particularly preferred for Y, the radicals chosen from the group consisting of a hydrogen or chlorine atom or the methoxy, —$OCH_2(CO)OH$ or —$OCH_2(CO)OMe$ group.

The group D may be chosen in particular from the imidazolinium, thiazolinium, oxazolinium, pyrrolinium, 1,2,3-triazolinium, 1,2,4-triazolinium, isoxazolinium, isothiazolinium, imidazolidinium, thiazolidinium, pyrazolinium, pyrazolidinium, oxazolidinium, pyrazoltriazolinium, pyrazoloimidazolinium, pyrrolotriazolinium, pyrazolopyrimidinium, pyrazolopyridinium, pyridinium, pyrimidinium, pyrazinium, triazinium, benzoimidazolinium, benzoxazolinium, benzothiazolinium, indolinium, indolidinium, isoindolinium, indazolinium, benzotriazolinium, quinolinium, tetrahydroquinolinium, benzoimidazolidinium, benzopyrimidinium, tetra($C_1$–$C_4$) alkylammonium, dialkylpiperidinium, dialkylpyrrolidinium, dialkylmorpholinium, dialkylthiomorpholinium, dialkylpiperazinium, azepinium and 1,4-diazabicyclo[2.2.2] octanium groups.

Still more preferably, the group D may be chosen from the 3-methylimidazolidinium-1-yl, 3-(2-hydroxyethyl) imidazolidinium-1-yl, 1,2,4-triazolinium-1-yl, 1,2,4-triazolinium-4-yl, N—($C_1$–$C_4$)alkylpyridinium-2-yl, N—($C_1$–$C_4$)alkylpyridinium-3-yl, N—($C_1$–$C_4$) alkylpyridinium-4-yl, N-(2-hydroxyethyl)pyridinium-2-yl, N-(2-hydroxyethyl)pyridinium-3-yl, N-(2-hydroxyethyl) pyridinium-4-yl, pyridinium-1-yl, trialkyl($C_1$–$C_4$) ammonium-N-yl, 1-methylpiperidinium-1-yl and 1,4-dimethylpiperazinium-1-yl groups.

Among the compounds of formula (I), there are particularly preferred those in which:

i)
the radical $R_1$ represents a radical chosen from the group (G5) consisting of an acetylamino, methanesulphonylamino, amido or methylamido radical, a group —NH—C(O)—$CH_2$—D1, a group —NH—$SO_2$—$CH_2$—$CH_2$—D1, a group —(CO)—NH—$CH_2$—$CH_2$—D1 in which D1 represents a 3-methylimidazolidinium-1-yl, triazolinium-1-yl, pyridinium-1-yl or trimethylammonium-N-yl group;
the radical $R_2$ is at the 5-position and represents a radical chosen from the group (G6) consisting of an amino, methylamino, acetylamino or methanesulphonylamino radical, a group —NH—$[C(O)]_m$—$CH_2$—D1 in which m represents 0 or 1, or a group —NH—$SO_2$—$CH_2$—$CH_2$—D1;
the radical $R_3$ represents a hydrogen atom;
the radical Y represents a radical chosen from the group (G7) consisting of a hydrogen atom, a chlorine radical and a methoxy radical; or ii)
the radical $R_1$ represents a radical chosen from the group (G5) as defined above;
the radical $R_2$ is situated at the 8-position and represents a radical chosen from the group (G6) as defined above;
the radical $R_3$ represents a hydrogen atom;
the radical Y represents a radical chosen from the group (G7) as defined above; or iii)
the radical $R_1$ represents a radical chosen from the group (G5) as defined above;
the radicals $R_2$ and $R_3$ represent a hydrogen atom;
the radical Y represents a radical chosen from the group (G7) as defined above.

Among the compounds of formula (I) in accordance with the invention, there may be mentioned most particularly:

3-[(1-Hydroxynaphthalen-2-ylcarbamoyl)methyl]-1-methyl-3H-imidazol-1-ium chloride;

3-[(1-Hydroxy-5-(2-(3-methyl-1H-imidazol-3-ium-1-yl) acetyl)aminonaphthalen-2-ylcarbamoyl)methyl]-1-methyl-3H-imidazol-1-ium dichloride;

3-[(1-Hydroxy-8-(2-(3-methyl-1H-imidazol-3-ium-1-yl) acetyl)aminonaphthalen-2-ylcarbamoyl)methyl]-1-methyl-3H-imidazol-1-ium dichloride;

3-[(1-Hydroxy-5-aminonaphthalen-2-ylcarbamoyl)methyl]-1-methyl-3H-imidazol-1-ium chloride;

3-[(1-Hydroxy-5-acetylaminonaphthalen-2-ylcarbamoyl) methyl]-1-methyl-3H-imidazol-1-ium chloride;

3-[(1-Hydroxy-5-methoxycarbonylaminonaphthalen-2-ylcarbamoyl)methyl]-1-methyl-3H-imidazol-1-ium chloride;

3-[(1-Hydroxy-2-acetylaminonaphthalen-5-ylcarbamoyl) methyl]-1-methyl-3H-imidazol-1-ium chloride;

3-[(1-Hydroxy-2-methoxycarbonylaminonaphthalen-5-ylcarbamoyl)methyl]-1-methyl-3H-imidazol-1-ium chloride;

3-[(1-Hydroxy-5-methanesulphonylaminonaphthalen-2-ylcarbamoyl)methyl]-1-methyl-3H-imidazol-1-ium chloride;

3-[(1-Hydroxy-8-aminonaphthalen-2-ylcarbamoyl)methyl]-1-methyl-3H-imidazol-1-ium chloride;

3-[(1-Hydroxy-8-acetylaminonaphthalen-2-ylcarbamoyl) methyl]-1-methyl-3H-imidazol-1-ium chloride;

3-[(1-Hydroxy-8-methoxycarbonylaminonaphthalen-2-ylcarbamoyl)methyl]-1-methyl-3H-imidazol-1-ium chloride;

3-[(1-Hydroxy-2-acetylaminonaphthalen-8-ylcarbamoyl) methyl]-1-methyl-3H-imidazol-1-ium chloride;

3-[(1-Hydroxy-2-methoxycarbonylaminonaphthalen-8-ylcarbamoyl)methyl]-1-methyl-3H-imidazol-1-ium chloride;

3-[(1-Hydroxy-8-methanesulphonylaminonaphthalen-2-ylcarbamoyl)methyl]-1-methyl-3H-imidazol-1-ium chloride;

1-[(1-Hydroxynaphthalen-2-ylcarbamoyl)methyl] pyridinium chloride;

1-[(1-Hydroxy-5-(2-(pyridinium-1-yl)acetyl) aminonaphthalen-2-ylcarbamoyl)methyl]pyridinium dichloride;

1-[(1-Hydroxy-8-(2-(pyridinium-1-yl)acetyl) aminonaphthalen-2-ylcarbamoyl)methyl]pyridinium dichloride;

1-[(1-Hydroxy-5-aminonaphthalen-2-ylcarbamoyl)methyl] pyridinium chloride;

1-[(1-Hydroxy-5-acetylaminonaphthalen-2-ylcarbamoyl) methyl]pyridinium chloride;

1-[(1-Hydroxy-5-methoxycarbonylaminonaphthalen-2-ylcarbamoyl)methyl]pyridinium chloride;

1-[(1-Hydroxy-2-acetylaminonaphthalen-5-ylcarbamoyl) methyl]pyridinium chloride;

1-[(1-Hydroxy-2-methoxycarbonylaminonaphthalen-5-ylcarbamoyl)methyl]pyridinium chloride;

1-[(1-Hydroxy-5-methanesulphonylaminonaphthalen-2-ylcarbamoyl)methyl]pyridinium chloride;
1-[(1-Hydroxy-8-aminonaphthalen-2-ylcarbamoyl)methyl]pyridinium chloride;
1-[(1-Hydroxy-8-acetylaminonaphthalen-2-ylcarbamoyl)methyl]pyridinium chloride;
1-[(1-Hydroxy-8-methoxycarbonylaminonaphthalen-2-ylcarbamoyl)methyl]pyridinium chloride;
1-[(1-Hydroxy-2-acetylaminonaphthalen-8-ylcarbamoyl)methyl]pyridinium chloride;
1-[(1-Hydroxy-2-methoxycarbonylaminonaphthalen-8-ylcarbamoyl)methyl]pyridinium chloride;
1-[(1-Hydroxy-8-methanesulphonylaminonaphthalen-2-ylcarbamoyl)methyl]pyridinium chloride;
1-[(1-Hydroxynaphthalen-2-ylcarbamoyl)methyl]-1,4-dimethylpiperazin-1-ium chloride;
1-[(1-Hydroxy-5-(2-(1,4-dimethylpiperazin-1-ium-1-yl)acetyl)aminonaphthalen-2-ylcarbamoyl)methyl]-1,4-dimethylpiperazin-1-ium dichloride;
1-[(1-Hydroxy-8-(2-(1,4-dimethylpiperazin-1-ium-1-yl)acetyl)aminonaphthalen-2-ylcarbamoyl)methyl]-1,4-dimethylpiperazin-1-ium dichloride;
1-[(1-Hydroxy-5-aminonaphthalen-2-ylcarbamoyl)methyl]-1,4-dimethylpiperazin-1-ium chloride;
1-[(1-Hydroxy-5-acetylaminonaphthalen-2-ylcarbamoyl)methyl]-1,4-dimethylpiperazin-1-ium chloride;
1-[(1-Hydroxy-5-methoxycarbonylaminonaphthalen-2-ylcarbamoyl)methyl]-1,4-dimethylpiperazin-1-ium chloride;
1-[(1-Hydroxy-2-acetylaminonaphthalen-5-ylcarbamoyl)methyl]-1,4-dimethylpiperazin-1-ium chloride;
1-[(1-Hydroxy-2-methoxycarbonylaminonaphthalen-5-ylcarbamoyl)methyl]-1,4-dimethylpiperazin-1-ium chloride;
1-[(1-Hydroxy-5-methanesulphonylaminonaphthalen-2-ylcarbamoyl)methyl]-1,4-dimethylpiperazin-1-ium chloride;
1-[(1-Hydroxy-8-aminonaphthalen-2-ylcarbamoyl)methyl]-1,4-dimethylpiperazin-1-ium chloride;
1-[(1-Hydroxy-8-acetylaminonaphthalen-2-ylcarbamoyl)methyl]-1,4-dimethylpiperazin-1-ium chloride;
1-[(1-Hydroxy-8-methoxycarbonylaminonaphthalen-2-ylcarbamoyl)methyl]-1,4-dimethylpiperazin-1-ium chloride;
1-[(1-Hydroxy-2-acetylaminonaphthalen-8-ylcarbamoyl)methyl]-1,4-dimethylpiperazin-1-ium chloride;
1-[(1-Hydroxy-2-methoxycarbonylaminonaphthalen-8-ylcarbamoyl)methyl]-1,4-dimethylpiperazin-1-ium chloride;
1-[(1-Hydroxy-8-methanesulphonylaminonaphthalen-2-ylcarbamoyl)methyl]-1,4-dimethylpiperazin-1-ium chloride;
and their addition salts with an acid.

These novel compounds of formula (I) may be prepared according to methods well known in the state of the art and described for example in Patent Applications or Patents JP95-303798, JP01186859, JP63258843 and DD285095.

The subject of the invention is also the use of the compounds of formula (I) as coupler for the oxidation dyeing of keratinous fibres and in particular human keratinous fibres such as hair.

Another subject of the invention is a composition for the oxidation dyeing of keratinous fibres, and in particular human keratinous fibres such as hair, characterized in that it contains, in a medium appropriate for dyeing:
at least one oxidation base, and
at least one coupler chosen from the compounds of formula (I) as defined above, as well as their addition salts with an acid.

The compound(s) of formula (I) in accordance with the invention and/or the or their addition salt(s) with an acid preferably represent from 0.0005 to 12% by weight approximately of the total weight of the dyeing composition and still more preferably from 0.005 to 6% by weight approximately of this weight.

As indicated above, the oxidation dyeing composition containing the compound(s) of formula (I) in accordance with the invention makes it possible to obtain intense colours in shades ranging from red to blue, and exhibiting, furthermore, remarkable resistance to the various treatments to which the keratinous fibres may be subjected. These properties are particularly remarkable in particular as regards the resistance of the colours obtained to the action of light, adverse weather conditions, washing, permanent waving and perspiration.

The nature of the oxidation base(s) which can be used in the dyeing composition in accordance with the invention is not critical. They are preferably chosen from the oxidation bases conventionally used in oxidation dyeing and among which there may be mentioned in particular para-phenylenediamines, bisphenylalkylenediamines, para-aminophenols, ortho-aminophenols and heterocyclic bases.

Among the para-phenylenediamines, there may be mentioned more particularly by way of example para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-amino-phenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines mentioned above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

Among the bisphenylalkylenediamines, there may be mentioned more particularly by way of example N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among the para-aminophenols, there may be mentioned more particularly by way of example para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols, there may be mentioned more particularly by way of example 2-aminophenol, 2-amino-5-methylphenol, 2-amino-6-methylphenol, 5-acetamido-2-aminophenol, and their addition salts with an acid.

Among the heterocyclic bases, there may be mentioned more particularly by way of example pyridine derivatives, pyrimidine derivatives and pyrazole derivatives.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-10659 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in Patent Application FR-A-2,750,048 and among which there may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine and their addition salts and their tautomeric forms, when a tautomeric equilibrium exists and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

According to the invention, the dyeing compositions containing one or more para-phenylenediamines and/or one or more heterocyclic oxidation bases are particularly preferred.

The oxidation base(s) preferably represent from 0.0005 to 12% by weight approximately of the total weight of the dyeing composition, and still more preferably from 0.005 to 6% by weight approximately of this weight.

The dyeing composition in accordance with the invention may also contain, in addition to the compound(s) of formula (I) above, one or more additional couplers which may be chosen from the couplers conventionally used in oxidation dyeing and among which there may be mentioned in particular meta-phenylenediamines, meta-aminophenols, meta-diphenols and heterocyclic couplers such as, for example, indole derivatives, indoline derivatives, pyridine derivatives and pyrazolones, and their addition salts with an acid.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, and their addition salts with an acid.

When they are present, these additional couplers preferably represent from 0.0001 to 10% by weight approximately of the total weight of the dyeing composition and still more preferably from 0.005 to 5% by weight approximately of this weight.

In general, the addition salts with an acid which can be used in the context of the dyeing compositions of the invention (compounds of formula (I), oxidation bases and additional couplers) are chosen in particular from hydrochlorides, hydrobromides, sulphates, citrates, succinates, tartrates, lactates and acetates.

The medium appropriate for dyeing (or carrier) generally consists of water or of a mixture of water and at least one organic solvent for solubilizing the compounds which might not be sufficiently soluble in water. By way of organic solvent, there may be mentioned for example lower $C_1$–$C_4$ alkanols such as ethanol and isopropanol; glycerol; glycols and glycol ethers such as 2-butoxyethanol, propylene glycol, monomethyl ether of propylene glycol, monoethyl ether and monomethyl ether of diethylene glycol, as well as aromatic alcohols such as benzyl alcohol or phenoxyethanol, similar products and mixtures thereof.

The solvents may be present in proportions preferably of between 1 and 40% by weight approximately relative to the total weight of the dyeing composition, and still more preferably between 5 and 30% by weight approximately.

The pH of the dyeing composition in accordance with the invention is generally between 3 and 12 approximately, and preferably between 5 and 11 approximately. It can be adjusted to the desired value by means of acidifying or alkalinizing agents normally used in dyeing keratinous fibres.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid and sulphonic acids.

Among the alkalinizing agents, there may be mentioned, by way of example, aqueous ammonia, alkali metal carbonates, alkanolamines such as mono-, di- and trietha nolamines as well as their derivatives, sodium or potassium hydroxides and the compounds of the following formula (V):

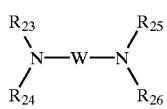

in which W is a propylene residue which is unsubstituted or substituted with a hydroxyl group or a $C_1$–$C_6$ alkyl radical; $R_{23}$, $R_{24}$, $R_{25}$ and $R_{26}$, which are identical or different, represent a hydrogen atom, a $C_1$–$C_6$ alkyl or $C_1$–$C_6$ hydroxyalkyl radical.

The oxidation dyeing compositions in accordance with the invention may also contain at least one direct dye, in particular for modifying the shades or enriching them with glints.

The dyeing composition in accordance with the invention may also contain various adjuvants conventionally used in hair dyeing compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetrating agents, sequestering agents, perfumes, buffers, dispersing agents, conditioning agents such as for example modified or unmodified, volatile or nonvolatile silicones, film-forming agents, ceramides, preservatives, opacifying agents.

Of course, persons skilled in the art will be careful to choose this or these possible additional compounds such that the advantageous properties which are intrinsically attached to the oxidation dyeing composition in accordance with the invention are not, or not substantially, impaired by the addition(s) envisaged.

The dyeing composition according to the invention may be provided in various forms, such as in the form of liquids, creams, gels, or in any other form appropriate for dyeing keratinous fibres, and in particular human hair.

The subject of the invention is also a method of oxidation dyeing of keratinous fibres, and in particular human keratinous fibres such as hair, using the dyeing composition as defined above.

According to this method, at least one dyeing composition as defined above is applied to the fibres, the colour being developed at acidic, neutral or alkaline pH with the aid of an oxidizing agent which is added just at the time of use to the dyeing composition or which is present in an oxidizing composition applied simultaneously or sequentially.

According to a preferred embodiment of the dyeing method of the invention, the dyeing composition described above is preferably mixed, at the time of use, with an oxidizing composition containing, in a medium appropriate for dyeing, at least one oxidizing agent present in a sufficient quantity to develop a colour. The mixture obtained is then applied to the keratinous fibres and allowed to act for 3 to 50 minutes approximately, preferably 5 to 30 minutes approximately, after which they are rinsed, washed with shampoo, rinsed again and dried.

The oxidizing agent may be chosen from the oxidizing agents conventionally used for the oxidation dyeing of keratinous fibres, and among which there may be mentioned hydrogen peroxide, urea peroxide, alkali metal bromates, persalts such as perborates and persulphates, and enzymes such as peroxidases, laccases, tyrosinases and oxidoreductases among which there may be mentioned in particular pyranose oxidases, glucose oxidases, glycerol oxidases, lactate oxidases, pyruvate oxidases and uricases.

The pH of the oxidizing composition containing the oxidizing agent as defined above is such that after mixing with the dyeing composition, the pH of the resulting composition applied to the keratinous fibres preferably varies between 3 and 12 approximately, and still more preferably between 5 and 11. It is adjusted to the desired value by means of acidifying or alkalinizing agents normally used for dyeing keratinous fibres and as defined above.

The oxidizing composition as defined above may also contain various adjuvants conventionally used in hair-dyeing compositions and as defined above.

The composition which is finally applied to the keratinous fibres may be provided in various forms, such as in the form of liquids, creams, gels or in any other form appropriate for dyeing keratinous fibres, and in particular human hair.

Another subject of the invention is a multicompartment device or dyeing "kit" or any other multicompartment packaging system in which a first compartment contains the dyeing composition as defined above and a second compartment contains the oxidizing composition as defined above. These devices may be equipped with a means which makes it possible to deliver the desired mixture to the hair, such as the devices described in Patent FR-2,586,913 in the name of the applicant.

The following examples are intended to illustrate the invention.

EXAMPLES OF PREPARATION

Example of Preparation 1

Synthesis of 3-[(1-hydroxynaphthalen-2-ylcarbamoyl)methyl]-1-methyl-3H-imidazol-1ium chloride

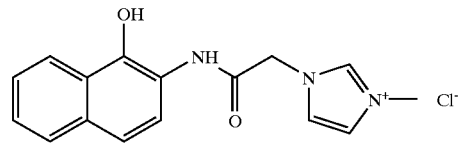

a) Preparation of 2-chloro-N-(1-hydroxynaphthalen-2-yl) acetamide 2 ml of chloroacetyl chloride (25.4 mmol) were added dropwise to a suspension of 5 g of 2-amino-1-naphthol hydrochloride (25.4 mmol) and 5.08 g of calcium carbonate in 200 ml of dioxane, with stirring and under an inert atmosphere. The reaction medium was stirred at 40° C. for 1 hour 30 minutes, cooled to 15° C., filtered on sintered glass and the inorganic salts were rinsed twice with ethyl acetate. The combined organic phases were concentrated until an insoluble product appeared. The concentrate was poured over 250 ml of ice-cold water. The precipitate formed was drained, washed with water and dried under vacuum to a constant weight to give 3.58 g of 2-chloro-N-(1-hydroxynaphthalen-2-yl)acetamide in the form of a beige powder with a yield of 60%.

b) Preparation of 3-[(1-hydroxynaphthalen-2-ylcarbamoyl) methyl]-1-methyl-3H-imidazol-1-ium chloride A solution of 2-chloro-N-(1-hydroxynaphthalen-2-yl) acetamide obtained above in the preceding step (2 g; 8.4 mmol) and N-methylimidazole (1.4 ml; 17 mmol) in 30 ml of tetrahydrofuran was heated under reflux for 5 hours. The precipitate formed was drained, washed twice with tetrahydrofuran and dried under vacuum to a constant weight to give 1.79 g of 3-[(1-hydroxynaphthalen-2-ylcarbamoyl) methyl]-1-methyl-3H-imidazol-1-ium chloride in the form of a beige powder with a yield of 67% and a melting point of 130° C.

The elemental analysis calculated for $C_{16}H_{16}N_3O_2C_1$ was the following:

| % | C | H | N | O | Cl |
|---|---|---|---|---|---|
| Found | 60.28 | 5.08 | 12.90 | 10.83 | 11.24 |
| Calculated | 60.48 | 5.08 | 13.22 | 10.07 | 11.16 |

Example of Preparation 2

Synthesis of 3-[(5-acetylamino-1-hydroxynaphthalen-2-ylcarbamoyl)methyl]-1-methyl-3H-imidazol-1-ium chloride

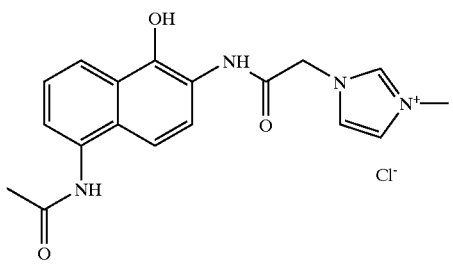

a) Preparation of N-(5-hydroxynaphthalen-1-yl)acetamide

To a solution of 5-amino-1-naphthol (17.6 g; 0.11 mol) in 500 ml of dioxane, there were added 11 g of calcium carbonate (0.11 mol) and, dropwise, 8 ml of chloroacetyl chloride (0.112 mol), with stirring and under an inert atmosphere. The reaction medium was heated at 80° C. for 2 hours 30 minutes. The suspension was cooled to room temperature, filtered on sintered glass and the inorganic salts were rinsed twice with dioxane. The mixture of the organic solutions was concentrated until an insoluble product appeared, and then poured over 400 ml of ice-cold water. The precipitate formed was drained, washed once with water and once with pentane. The brown powder obtained was dried under vacuum to a constant weight to give 16.8 g of N-(5-hydroxynaphthalen-1-yl)acetamide with a yield of 76%.

b) Preparation of N-(5-hydroxy-6-nitrosonaphthalen-1-yl)acetamide

A brown solution of N-(5-hydroxynaphthalen-1-yl) acetamide obtained above in the preceding step (25 g, 0.124 mol) and anhydrous zinc chloride (25 g, 0.183 mol) in 125 ml of ethanol was heated to 50° C. A solution of sodium nitrite (8.75 g, 0.127 mol) in 17.5 ml of water was introduced dropwise into the suspension. The reaction medium was heated at 60° C. for 2 hours and then cooled to 20° C. and the precipitate formed was drained, washed three times with ethanol and then poured in small spatula amounts over 50 ml of hydrochloric acid (35%), with stirring, at 15° C. The medium was stirred for 1 hour and then 50 ml of water at 2° C. were slowly added. The precipitate was drained and washed 4 times with water. The green powder obtained was dried under vacuum to a constant weight to give 24.4 g of N-(5-hydroxy-6-nitrosonaphthalen-1-yl)acetamide with a yield of 86%.

c) Preparation of N-(5-hydroxy-6-aminonaphthalen-1-yl) acetamide 3 g of N-(5-hydroxy-6-nitroso-naphthalen-1-yl)acetamide obtained above in the preceding step (13 mmol) were dissolved in 30 ml of a 10% aqueous sodium hydroxide solution. The reaction medium was cooled to 15° C. and sodium hydrosulphite (7 g, 67 mmol) was added in small spatula amounts, while the temperature was maintained at 15–20° C. The reaction medium was cooled to 0° C. and the pH adjusted to pH=7.05 with 5.5 ml of a 6N hydrochloric acid solution. The precipitate was drained, washed three times with water and dried under vacuum to constant weight to give 1.7 g of N-(5-hydroxy-6-aminonaphthalen-1-yl) acetamide with a yield of 59%.

d) Preparation of N-(5-acetylamino-1-hydroxynaphthalen-2-yl)-2-chloroacetamide 0.48 ml of chloroacetyl chloride (6 mmol) was introduced into a suspension of 1.3 g of N-(5-hydroxy-6-aminonaphthalen-1-yl)acetamide obtained above in step c) (6 mmol) and 0.6 g of calcium carbonate (6 mmol) in 50 ml of dioxane, with stirring and under an inert atmosphere. The reaction medium was stirred for 3 hours under reflux and then cooled to 30° C. The reaction medium was diluted with 400 ml of water and extracted three times with 200 ml of ethyl acetate. The combined organic phases were dried over sodium sulphate and concentrated to dryness to give 0.67 g of N-(5-acetylamino-1-hydroxynaphthalen-2-yl)-2-chloroacetamide in the form of a pink powder, with a yield of 38%.

e) Preparation of 3-[(1-hydroxy-5-acetylaminonaphthalen-2-ylcarbamoyl)methyl]-1-methyl-3H-imidazol-1-ium chloride 0.25 ml of N-methylimidazole (3.1 mmol) was introduced into a solution of N-(5-acetylamino-1-hydroxynaphthalen-2-yl)-2-chloroacetamide obtained above in step d) (0.9 g, 3 mmol) in 20 ml of dioxane. The reaction medium was heated under reflux for 7 hours and 30 minutes. The precipitate formed was drained, washed abundantly with dioxane and dried under vacuum to constant weight to give 0.82 g of 3-[(1-hydroxy-5-acetylaminonaphthalen-2-ylcarbamoyl) methyl]-1-methyl-3H-imidazol-1-ium chloride in the form of a red powder melting at 168° C. and with a yield of 73%. Cation mass spectroscopy analysis: m/z=338 of the product obtained was consistent with that of the product obtained.

Example of Preparation 3

Synthesis of 3-[(1-hydroxy-5-methanesulphonylaminonaphthalen-2-ylcarbamoyl) methyl]-1-methyl-3H-imidazol-1-ium chloride

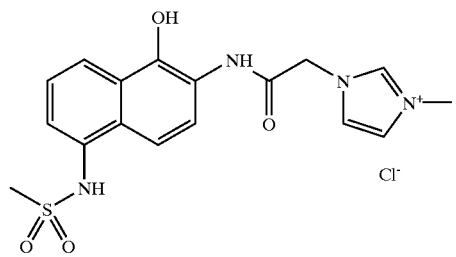

a) Preparation of N-(5-methanesulphonylamino-1-hydroxynaphthalen-2-yl)-2-chloroacetamide 0.32 ml of chloroacetyl chloride (4 mmol) was introduced into a suspension of 1 g of N-(5-hydroxy-6-aminonaphthalen-1-yl)methanesulphonamide (4 mmol, prepared according to the method described in Patent U.S. Pat. No. 4,956,456) and 0.4 g of calcium carbonate (4 mmol) in 50 ml of dioxane, with stirring and under an inert atmosphere. The reaction medium was stirred for 2 hours at 85° C. and then cooled to 30° C. The suspension was filtered on sintered glass and the inorganic salts were rinsed twice with a minimum of dioxane. The combined organic phases were poured over 100 ml of ice-cold water. The precipitate formed was drained, washed twice with water and dried under vacuum to constant weight to give 1.12 g of N-(5-methanesulphonylamino-1-hydroxynaphthalen-2-yl)-2-chloroacetamide in the form of a pink powder, with a yield of 84%.

b) Preparation of 3-[(1-hydroxy-5-methanesulphonylaminonaphthalen-2-ylcarbamoyl)methyl]-1-methyl-3H-imidazol-1-ium chloride 0.25 ml of N-methylimidazole (3.1 mmol) was introduced into a solution of N-(5-methanesulphonylamino-1-hydroxynaphthalen-2-yl)-2-chloroacetamide obtained above in the preceding step (1 g, 3 mmol) in 20 ml of tetrahydrofuran. The reaction medium was heated under reflux for 8 hours. The precipitate formed was drained, washed abundantly with dioxane and dried under vacuum to constant weight to give 0.86 g of 3-[(1-hydroxy-5-methanesulphonylaminonaphthalen-2-ylcarbamoyl)methyl]-1-methyl-3H-imidazol-1-ium chloride in the form of a brown powder melting at 198° C., with a yield of 70%. The cation mass spectroscopy analysis: m/z=375 of the product obtained was consistent with that of the expected product.

EXAMPLES OF APPLICATION

Examples of Dyeing 1 to 7 in Alkaline Medium

The following dyeing compositions in accordance with the invention were prepared, (contents in grams):

The shades obtained are presented in the table below:

| EXAMPLE | Dyeing pH | Shade obtained |
|---|---|---|
| 1 | 10 ± 0.2 | Slightly purple light chestnut brown |
| 2 | 10 ± 0.2 | Slightly iridescent dark purple light chestnut brown |
| 3 | 10 ± 0.2 | Blue |
| 4 | 10 ± 0.2 | Ash chestnut brown |
| 5 | 10 ± 0.2 | Copper iridescent dark blond |
| 6 | 10 ± 0.2 | Slightly iridescent dark purple chestnut brown |
| 7 | 10 ± 0.2 | Slightly ash blue |

| EXAMPLE | 1 | 2 | 3 | 4 | 5 | 6 | 7 |
|---|---|---|---|---|---|---|---|
| 3-[(1-Hydroxynaphthalen-2-ylcarbamoyl)methyl]-1-methyl-3H-imidazo1-1-ium chloride (compound of formula (I)) | 0.96 | 0.96 | 0.96 | — | — | — | — |
| 3-[(5-Acetylamino-1-hydroxynaphthalen-2-ylcarbamoyl)methyl]-1-methyl-3H-imidazol-1-ium chloride (compound of formula (I)) | — | — | — | 1.13 | 1.13 | — | — |
| 3-[(1-Hydroxy-5-methanesulphonylaminonaphthalen-2-ylcarbamoyl)methyl]-1-methyl-3H-imidazol-1-ium chloride (compound of formula (I)) | — | — | — | — | — | 1.24 | 1.24 |
| 4,5-Diamino-1-ethyl-3-methylpyrazole dihydrochloride (oxidation base) | 0.639 | — | — | — | — | — | — |
| Pyrazolo[1,5-a]pyrimidine-3,7-diamine.2HCl (oxidation base) | — | 0.666 | — | — | — | 0.666 | — |
| N,N-Bishydroxyethyl-para-phenylenediamine.2HCl (oxidation base) | — | — | 0.882 | — | — | — | 0.882 |
| para-Phenylenediamine (oxidation base) | — | — | — | 0.324 | — | — | — |
| para-Aminophenol (oxidation base) | — | — | — | — | 0.327 | — | — |
| Common dyeing carrier No. 1 | (*) | (*) | (*) | (*) | (*) | (*) | (*) |
| Demineralized water qs | 100 g | 100 g | 100 g | 100 g | 100 g | 100 g | 100 g |

(*)Common dyeing carrier No. 1:

Benzyl alcohol 2.0 g
Polyethylene glycol containing 6 mol of ethylene oxide 3.0 g
Ethanol, 96% 20.0 g
($C_8$–$C_{10}$)alkylpolyglucoside in aqueous solution containing 60% of active substance (AS), buffered with ammonium citrate, sold under the name Oramix CG 110® by the company Seppic 6.0 g
Aqueous ammonia containing 20% of $NH_3$ 10.0 g
Sodium metabisulphite containing 35% of active substance 0.228 g
Pentasodium salt of diethylenetriaminopentaacetic acid 1.1 g At the time of use, each of the above dyeing compositions was mixed weight for weight with a solution of hydrogen peroxide containing 20 volumes (6% by weight) 5 of pH 3.

The mixture obtained was applied to locks of natural grey hair which is 90% white for 30 minutes. The locks were then rinsed, washed with a standard shampoo, rinsed again and then dried.

What is claimed is:

1. A compound of the following formula (I) or an acid addition salt thereof;

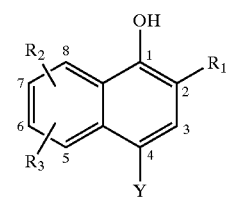

wherein:
$R_1$ represents a group chosen from —$NR_4$(C=O)$R_5$, —$NR_6SO_2R_7$ and —(C=O)$NR_6R_8$, the radicals $R_4$, $R_5$, $R_6$, $R_7$ and $R_8$ being as defined below;
$R_2$ and $R_3$, which are identical or different, represent a hydrogen atom; a halogen atom; a group Z as defined below; or a radical comprising from 1 to 20 carbon atoms, wherein the radical is linear or branched, wherein the branch(es) may form one or more carbon-containing rings comprising from 3 to 7 members, wherein the radical may contain bonds chosen from one or more double bonds and one or more triple bonds, wherein the double bonds may lead to aromatic groups, wherein one or more carbon atoms of the radical may be replaced with an oxygen, nitrogen or sulphur atom or with an $SO_2$ group, and in which the carbon atoms may, independently of each other, be substituted with one or more halogen atoms; it being understood that:

the said radicals $R_2$ and $R_3$ cannot be linked to the benzene ring of formula (I) by an —NH—NH— bond; and $R_2$ and $R_3$ do not contain a peroxide bond or diazo, nitro and nitroso radicals;

$R_2$ and $R_3$ cannot represent a hydroxyl radical or a thio radical;

$R_2$ and $R_3$ cannot each represent, simultaneously, an amino, alkylamino, acylamino or sulphonylamino radical;

Y represents a hydrogen or halogen atom; a group —$OR_9$, —$SR_9$, or —NH—$SO_2R_9$ in which $R_9$ represents a $C_1$–$C_6$ alkyl radical, linear or branched, wherein the branch(es) may form one or more rings comprising from 3 to 6 members, wherein the radical may be unsubstituted or substituted with one or more radicals chosen from halogen atoms, hydroxyl radicals, and $C_1$–$C_4$ alkoxy, amino, and amino($C_1$–$C_4$ alkyl) radicals; a phenyl radical, wherein the phenyl radical may be unsubstituted or substituted with one or two radicals chosen from $C_1$–$C_4$ alkyl, trifluoromethyl, carboxyl, $C_1$–$C_4$ alkoxycarbonyl, halogen, hydroxyl, $C_1$–$C_4$ alkoxy, amino, and amino($C_1$–$C_4$ alkyl) radicals; or a benzyl radical;

$R_4$, $R_6$ and $R_8$, which are identical or different, represent a hydrogen atom; a group Z as defined below; or a radical comprising from 1 to 15 carbon atoms, linear or branched, wherein the branch(es) may form one or more carbon-containing rings comprising from 3 to 7 members, wherein the radical may contain bonds chosen from one or more double bonds and one or more triple bonds, wherein the double bonds may lead to aromatic groups, wherein one or more carbon atoms in the radical may be replaced with an oxygen, nitrogen, or sulphur atom or with an $SO_2$ group, and in which the carbon atoms may, independently of each other, be substituted with one or more halogen atoms;

it being understood that the $SO_2$ group is not directly linked to the nitrogen atom carrying the radical $R_4$ or $R_6$;

it being understood that the —(C=O)— group is not directly linked to the nitrogen atom carrying the radical $R_6$;

it being understood that the radicals $R_4$, $R_6$ and $R_8$ do not contain a peroxide bond or diazo, nitro and nitroso radicals; it being understood that the radicals $R_4$, $R_6$ and $R_8$ cannot represent a hydroxyl radical, a thio radical, an amino radical, an alkoxy radical, or an alkylthio radical;

$R_5$ and $R_7$, which are identical or different, represent a hydrogen atom; a group Z as defined below; or a radical comprising from 1 to 20 carbon atoms, wherein the radical may be linear or branched, wherein the branch (es) may form one or more carbon-containing rings comprising from 3 to 7 members, wherein the radical may contain bond chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms;

it being understood that the said radicals $R_5$ and $R_7$ do not contain peroxide bonds or diazo, nitro and nitroso radicals;

it being understood that $R_5$ cannot represent a hydroxyl radical or a thio radical;

it being understood that $R_7$ cannot represent a thio radical;

it being understood that the radicals $R_4$ and $R_5$ on the one hand, and the radicals $R_6$ and $R_8$ on the other hand, can, in addition, be linked to form, independently of each other, a saturated or unsaturated ring comprising from 5 to 7 members, the members being chosen from carbon, nitrogen and acyl, each member being unsubstituted or substituted with 1 or 2 radicals R, which are identical or different, R being a $C_1$–$C_8$ alkyl radical, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms; the said ring containing no peroxide bonds or diazo, nitro and nitroso radicals;

Z is a cationic group represented by the following formula (II):

wherein:

n can take the value 0 or 1;

B represents an alkyl radical comprising from 1 to 15 carbon atoms, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, and wherein one or more carbon atoms in the radical may be replaced with an oxygen, nitrogen or sulphur atom or with an —$SO_2$ radical; and wherein one or more carbon atoms in the radical may, independently of each other, be substituted with one or more halogen atoms or with one or more groups Z; the said radical B containing no peroxide bond or diazo, nitro, or nitroso radicals;

D is chosen from the cationic groups of the following formulae (III) and (IV):

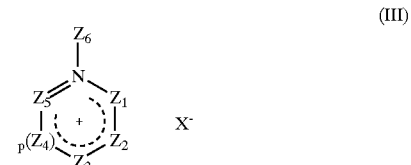

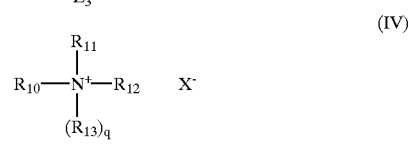

wherein:
p and q can, independently of each other, take the value 0 or 1;
the radical B is linked to the group D by any one of the atoms of the radical D;
when n=0 and q=0, then the group of formula (IV) can be linked to the compound of formula (I) directly by the nitrogen atom of the quaternary ammonium;
$Z_1$, $Z_2$, $Z_3$ and $Z_4$, independently of each other, represent an oxygen atom; a sulphur atom; a nitrogen atom which is unsubstituted or substituted with a radical $R_{14}$; or a carbon atom which is unsubstituted or substituted with one or two radicals $R_{14}$, which are identical or different;
$Z_5$ represents a nitrogen atom or a carbon atom which is unsubstituted or substituted with a radical $R_{14}$;
$Z_6$ can have the same meanings as those indicated below for the radical $R_{14}$; it being understood that $Z_6$ is different from a hydrogen atom;
the radicals $Z_1$ or $Z_5$ can, in addition, form with $Z_6$ a saturated or unsaturated ring comprising from 5 to 7 members, each member being unsubstituted or substituted with one or two radicals $R_{14}$ which are identical or different;
$R_{14}$ represents a hydrogen atom; a group Z; or a radical comprising from 1 to 10 carbon atoms, linear or branched, which may contain bonds chosen from one or more double bonds and one or more triple bonds, wherein the double bonds may lead to aromatic groups, wherein one or more carbon atoms of the radical may be replaced with an oxygen, nitrogen or sulphur atom, or with an $SO_2$ group, and wherein one or more carbon atoms of the radical may, independently of each other, be substituted with one or more halogen atoms; the said radical containing no peroxide bond or diazo, nitro and nitroso radicals;
it being possible, in addition, for two of the adjacent radicals $Z_1$, $Z_2$, $Z_3$, $Z_4$ and $Z_5$ to form a ring comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;
$R_{10}$, $R_{11}$, $R_{12}$ and $R_{13}$, which are identical or different, have the same meanings as those indicated above for the radical $R_{14}$;
it being possible for the radicals $R_{10}$, $R_{11}$, $R_{12}$ and $R_{13}$ to also form, in pairs with the quaternary nitrogen atom to which they are attached, one or more saturated rings comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;
$X^-$ represents an organic or inorganic anion;
with the proviso that at least one of the groups $R_1$ to $R_3$ represents or contains a group Z.

2. A compound according to claim 1, wherein $R_2$ and $R_3$ represent, independently of each other, a hydrogen or chlorine atom; a group Z; a methyl or methoxy radical; an amino, methylamino, 2-hydroxyethylamino radical; a group —NH(CO)$R_{15}$ in which $R_{15}$ represents a radical chosen from methyl, ethyl, propyl, isopropyl, butyl, isobutyl, tert-butyl, pentyl, isopentyl, neopentyl, hexyl, cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl, phenyl, methylphenyl; dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenyl-vinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, pyridinyl, chloropyridinyl, dichloropyridinyl, 5-(bromo)pyridin-3-yl, piperazin-2-yl, 2-chloro-4-(trifluoromethyl)pyperimidin-5-yl, quinoxal-2-yl, benzofurazan-5-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloro-ethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, (methoxycarbonyl)methyl, 2-carboxyethyl, 2-(methoxycarbonyl)ethyl, 2-carboxycyclopropyl, 2-carboxycyclohexane, methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl radicals; or a group —$NHSO_2R_{16}$ in which $R_{16}$ represents a radical chosen from methyl, trifluoromethyl, ethyl, 2-chloroethyl, propyl, 3-chloropropyl, isopropyl, butyl, thiophen-2-yl, hydroxyl, ethoxy, amino and dimethylamino radicals.

3. A compound according to claim 2, wherein $R_2$ and $R_3$, independently of each other, are chosen from a hydrogen atom; a group —O—E—D', —NH—E—D', —NH(CO)—D', —NH(CO)—E—D', —NH(CO)O—E—D', —NH(CO)NH—E—D' or —NH(SO_2)—E—D', in which —E— represents a —$(CH_2)_q$— arm, q is an integer equal to 1 or 2, and in which D' is chosen from 3-methylimidazolidinium-1-yl, 3-(2-hydroxyethyl)imidazolidinium-1-yl, 1,2,4-triazolinium-1-yl, 1,2,4-triazolinium-4-yl, N—(C_1–C_4)alkylpyridinium-2-yl, N—(C_1–C_4)alkylpyridinium-3-yl, N—(C_1–C_4)alkylpyridinium-4-yl, N—(2-hydroxyethyl)-pyridinium-2-yl, N—(2-hydroxyethyl)pyridinium-3-yl, N—(2-hydroxyethyl)pyridinium-4-yl, pyridinium-1-yl, tri ($C_1$–$C_4$ alkyl)ammonium-N-yl, 1-methylpiperidinium-1-yl and 1,4-dimethyipiperazinium-1-yl groups; a methyl, methoxy, amino or methylamino radical; or a group —NH(CO)$R_{17}$ in which $R_{17}$ represents a radical chosen from methyl, trifluoromethyl, ethyl, 2-chloroethyl, propyl, 3-chloropropyl, isopropyl, butyl, thiophen-2-yl, hydroxyl, ethoxy, amino and dimethylamino radicals; or a methanesulphonylamino, ethanesulphonylamino or dimethylaminosulphonylamino group.

4. A compound according to claim 1, wherein $R_4$ represents a hydrogen atom or a group $A_1$ chosen from linear and branched $C_1$–$C_8$ alkyl radicals which may carry one or two double bonds or one triple bond, which may be unsubstituted or substituted with a group chosen from a group $A_2$, a group $A_4$, a group $A_5$, as defined below which may be unsubstituted or substituted with one or two groups, which are identical or different, chosen from N—($C_1$–$C_3$)alkylamino, N—($C_1$–$C_3$)alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano and carboxyl groups, and which may be unsubstituted or substituted with one or more hydroxyl, fluoro or chloro groups; group $A_2$ chosen from phenyl and naphthyl aromatic groups, which may be unsubstituted or substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups; group $A_3$ chosen from heteroaromatic groups chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazolo-imidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl groups, the said heteroaromatic groups being unsubstituted or substituted with 1 to 3 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical; group $A_4$ chosen from $C_3$–$C_7$ cycloalkyl radicals, a norbonyl radical, which may contain a double bond and which may be unsubstituted or substituted with 1 or 2 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical; or group $A_5$ chosen from heterocycles chosen from dihydrofuranyl, tetrahydrofuranyl, butyrolactonyl, dihydrothiophenyl, tetrahydrothiophenyl, tetrahydrothiophenonyl, iminothiolane, dihydropyrrolyl, pyrrolidinyl, pyrrolidinonyl, imidazolidinonyl, imidazolidinethionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridinyl, piperidinyl, pentalactam, morpholinyl, pyrazoli(di)nyl, pyrimi(di)nyl, pyrazinyl, piperazinyl and azepinyl rings; wherein the groups $A_1$, $A_2$, $A_3$, $A_4$ and $A_5$ are each optionally separated from the nitrogen of the group —N$R_4$(C=O)$R_5$ by a group —(CO)—.

5. A compound according to claim 4 wherein $R_4$ represents a hydrogen atom; a methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy)benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; or a 2-hydroxyethyl, 2-methoxyethyl or 2-ethoxyethyl group.

6. A compound according to claim 1, wherein $R_5$ denotes a hydrogen atom, an amino group; a group Z; a group $A_1$, $A_2$, $A_3$, $A_4$ or $A_5$, optionally separated from the carbon at the 2-position with respect to the amide function of formula (I) by a group chosen from —O—, —NH, —N($C_1$–$C_3$)alkyl- and —(CO)—; wherein group $A_1$ is chosen from linear and branched $C_1$–$C_8$ alkyl radical which may carry one or two double bonds or one triple bond, which may be unsubstituted or substituted with a group chosen from a group $A_2$, a group $A_4$, a group $A_5$, as defined below which may be unsubstituted or substituted with one or two groups, which are identical or different, chosen from the N—($C_1$–$C_3$)alkylamino, N—($C_1$–$C_3$)alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano and carboxyl groups, and which may be unsubstituted or substituted with one or more hydroxyl, fluoro or chloro groups;

group $A_2$ is chosen from phenyl and naphthyl aromatic groups, which may be unsubstituted or substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups;

group $A_3$ is chosen from heteroaromatic groups chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazolo-imidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl groups, the said heteroaromatic groups being unsubstituted or substituted with 1 to 3 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical;

group $A_4$ is chosen from $C_3$–$C_7$ cycloalkyl radicals, a norbonyl radical, which may contain a double bond and which may be unsubstituted or substituted with 1 or 2 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical; and group $A_5$ is chosen from heterocycles chosen from dihydrofuranyl, tetrahydrofuranyl, butyrolactonyl, dihydrothiophenyl, tetrahydrothiophenyl, tetrahydrothiophenonyl, iminothiolane, dihydropyrrolyl, pyrrolidinyl, pyrrolidinonyl, imidazolidinonyl, imidazolidinethionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridinyl, piperidinyl, pentalactam, morpholinyl, pyrazoli(di)nyl, pyrimi(di)nyl, pyrazinyl, piperazinyl and azepinyl rings.

7. A compound according to claim 6, wherein $R_5$ represents a group Z; a radical chosen from methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl radicals.

8. A compound according to claim 7, wherein $R_5$ represents a group chosen from —D', —E—D', —O—E—D' and —NH—E—D' in which —E— represents a —$(CH_2)_q$— arm, q is an integer equal to 1 or 2 and D' is chosen from 3-methylimidazolidinium-1-yl, 3-(2-hydroxyethyl) imidazolidinium-1-yl, 1,2,4-triazolinium-1-yl, 1,2,4-triazolinium-4-yl, N—$(C_1-C_4)$alkylpyridinium-2-yl, N—$(C_1-C_4)$alkylpyridinium-3-yl, N—$(C_1-C_4)$alkylpyridinium-4-yl, N-(2-hydroxyethyl)-pyridinium-2-yl, N—(2-hydroxyethyl)pyridinium-3-yl, N—(2-hydroxyethyl) pyridinium-4-yl, pyridinium-1-yl, tri$(C_1-C_4$ alkyl) ammonium-N-yl, 1-methylpiperidinium-1-yl and 1,4-dimethyipiperazinium-1-yl groups; or a radical chosen from methyl, methoxymethyl, 2-carboxyethyl, methoxy, amino, ethylamino and 1-pyrrolidinyl radicals.

9. A compound according to claim 1, wherein $R_4$ and $R_5$ form a ring, the ring being chosen from 2-pyrrolidinon-1-yl, methyl-2-pyrrolidinon-1-yl, 5-carboxy-2-pyrrolidinon-1-yl, 5-methoxycarbonyl-2-pyrrolidinon-1-yl, pyrazolinon-1-yl, succinimid-1-yl, 3,5-diketopyrazolidin-1-yl, oxindolin-1-yl, maleimid-1-yl, isoindole-1,3-dion-2-yl, 2-piperidinon-1-yl and glutarimid-1-yl groups.

10. A compound according to claim 1, wherein $R_6$ represents a hydrogen atom or a group $A_1$, $A_2$, $A_3$, $A_4$ or $A_5$; wherein group $A_1$ is chosen from linear and branched $C_1-C_8$ alkyl radical which may carry one or two double bonds or one triple bond, which may be unsubstituted or substituted with a group chosen from a group $A_2$, a group $A_4$, a group $A_5$, as defined below which may be unsubstituted or substituted with one or two groups, which are identical or different, chosen from the N—$(C_1-C_3)$ alkylamino, N—$(C_1-C_3)$alkyl-N—$(C_1-C_3)$ alkylamino, $(C_1-C_6)$alkoxy, oxo, alkoxycarbonyl, acyloxy, amide, acylamino, ureyl, sulphoxy, sulphonyl, sulphonamido, sulphonylamino, bromo, cyano and carboxyl groups, and which may be unsubstituted or substituted with one or more hydroxyl, fluoro or chloro groups;

group $A_2$ is chosen from phenyl and naphthyl aromatic groups, which may be unsubstituted or substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups;

group $A_3$ is chosen from heteroaromatic groups chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazolo-imidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl groups, the said heteroaromatic groups being unsubstituted or substituted with 1 to 3 radicals chosen from a linear or branched $C_1-C_4$ alkyl radical, a $C_1-C_4$ monohydroxyalkyl radical, a $C_2-C_4$ polyhydroxyalkyl radical, a carboxyl radical, an alkoxycarbonyl radical, a halogen atom, an amido radical, an amino radical and a hydroxyl radical;

group $A_4$ is chosen from $C_3-C_7$ cycloalkyl radicals, a norbonyl radical, which may contain a double bond and which may be unsubstituted or substituted with 1 or 2 radicals chosen from a linear or branched $C_1-C_4$ alkyl radical, a $C_1-C_4$ monohydroxyalkyl radical, a $C_2-C_4$ polyhydroxyalkyl radical, a carboxyl radical, an alkoxycarbonyl radical, a halogen atom, an amido radical, an amino radical and a hydroxyl radical; and group $A_5$ is chosen from heterocycles chosen from dihydrofuranyl, tetrahydrofuranyl, butyrolactonyl, dihydrothiophenyl, tetrahydrothiophenyl, tetrahydrothiophenonyl, iminothiolane, dihydropyrrolyl, pyrrolidinyl, pyrrolidinonyl, imidazolidinonyl, imidazolidinethionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridinyl, piperidinyl, pentalactam, morpholinyl, pyrazoli(di)nyl, pyrimi(di)nyl, pyrazinyl, piperazinyl and azepinyl rings.

11. A compound according to claim 10, wherein $R_6$ represents a hydrogen atom; a methyl, ethyl, isopropyl, allyl; phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; a 2-hydroxyethyl, 2-methoxyethyl or 2-ethoxyethyl group.

12. A compound according claim 1, wherein $R_8$ denotes a group Z; a hydrogen atom or a group $A_1$, $A_2$, $A_3$, $A_4$ or $A_5$; wherein group $A_1$ is chosen from linear and branched $C_1-C_8$ alkyl radical which may carry one or two double bonds or one triple bond, which may be unsubstituted or substituted with a group chosen from a group $A_2$, a group $A_4$, a group $A_5$, as defined below which may be unsubstituted or substituted with one or two groups, which are identical or different, chosen from the N—$(C_1-C_3)$ alkylamino, N—$(C_1-C_3)$alkyl-N—$(C_1-C_3)$ alkylamino, $(C_1-C_6)$alkoxy, oxo, alkoxycarbonyl, acyloxy, amide, acylamino, ureyl, sulphoxy, sulphonyl, sulphonamido, sulphonylamino, bromo, cyano and carboxyl groups, and which may be unsubstituted or substituted with one or more hydroxyl, fluoro or chloro groups;

group $A_2$ is chosen from phenyl and naphthyl aromatic groups, which may be unsubstituted or substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups;

group $A_3$ is chosen from heteroaromatic groups chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazolo-imidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl groups, the said heteroaromatic groups being unsubstituted or substituted with 1 to 3 radicals chosen from a linear or branched $C_1-C_4$ alkyl radical, a $C_1-C_4$ monohydroxyalkyl radical, a $C_2-C_4$ polyhydroxyalkyl radical, a carboxyl radical, an alkoxycarbonyl radical, a halogen atom, an amido radical, an amino radical and a hydroxyl radical;

group $A_4$ is chosen from $C_3$–$C_7$ cycloalkyl radicals, a norbonyl radical, which may contain a double bond and which may be unsubstituted or substituted with 1 or 2 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical; and group $A_5$ is chosen from heterocycles chosen from dihydrofuranyl, tetrahydrofuranyl, butyrolactonyl, dihydrothiophenyl, tetrahydrothiophenyl, tetrahydrothiophenonyl, iminothiolane, dihydropyrrolyl, pyrrolidinyl, pyrrolidinonyl, imidazolidinonyl, imidazolidinethionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridinyl, piperidinyl, pentalactam, morpholinyl, pyrazoli(di)nyl, pyrimi(di)nyl, pyrazinyl, piperazinyl and azepinyl rings.

13. A compound according to claim 12, wherein $R_8$ represents a group Z; a hydrogen atom; a methyl, ethyl, isopropyl, allyl; phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy)benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; a 2-hydroxyethyl, 2-methoxyethyl or 2-ethoxyethyl group.

14. A compound according to claim 13, wherein $R_8$ represents a hydrogen atom or a methyl radical; or a group —D' or a group —E—D', in which —E— represents a —$(CH_2)_q$—arm, q is an integer equal to 1 or 2, and D' is chosen from 3-methylimidazolidinium-1-yl, 3-(2-hydroxyethyl)imidazolidinium-1-yl, 1,2,4-triazolinium-1-yl, 1,2,4-triazolinium-4-yl, N—($C_1$–$C_4$)alkylpyridinium-2-yl, N—($C_1$–$C_4$)alkylpyridinium-3-yl, N—($C_1$–$C_4$) alkylpyridinium-4-yl, N-(2-hydroxyethyl)-pyridinium-2-yl, N-(2-hydroxyethyl)pyridinium-3-yl, N-(2-hydroxyethyl) pyridinium-4-yl, pyridinium-1-yl, tri($C_1$–$C_4$ alkyl) ammonium-N-yl, 1-methylpiperidinium-1-yl and 1,4-dimethyipiperazinium-1-yl groups.

15. A compound according to claim 1, wherein $R_6$ and $R_8$ form a ring chosen from pyrrolidinyl, piperidinyl, morpholinyl, pyrazolyl, isoxazolyl, imidazolyl, thiazolyl, indolyl, indolidinyl, indazolyl, pyrazolotriazolyl, pyrrolotriazolyl, pyrazoloimidazolyl, pyrazolidinyl, thiomorpholinyl, thiazolyl and pyrazinyl groups.

16. A compound according to claim 1, wherein $R_7$ denotes an amino group; a group Z; a group $A_1$, $A_2$, $A_3$, $A_4$ or $A_5$, optionally separated from the sulphur of the sulphonyl group of the compound of formula (I) by a group —NH or N($C_1$–$C_3$)alkyl-; wherein group $A_1$ is chosen from linear and branched $C_1$–$C_8$ alkyl radical which may carry one or two double bonds or one triple bond, which may be unsubstituted or substituted with a group chosen from a group $A_2$, a group $A_4$, a group $A_5$, as defined below which may be unsubstituted or substituted with one or two groups, which are identical or different, chosen from the N—($C_1$–$C_3$) alkylamino, N—($C_1$–$C_3$)alkyl-N—($C_1$–$C_3$) alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano and carboxyl groups, and which may be unsubstituted or substituted with one or more hydroxyl, fluoro or chloro groups;

group $A_2$ is chosen from phenyl and naphthyl aromatic groups, which may be unsubstituted or substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups;

group $A_3$ is chosen from heteroaromatic groups chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazolo-imidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl groups, the said heteroaromatic groups being unsubstituted or substituted with 1 to 3 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical;

group $A_4$ is chosen from $C_3$–$C_7$ cycloalkyl radicals, a norbonyl radical, which may contain a double bond and which may be unsubstituted or substituted with 1 or 2 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical; and group $A_5$ is chosen from heterocycles chosen from dihydrofuranyl, tetrahydrofuranyl, butyrolactonyl, dihydrothiophenyl, tetrahydrothiophenyl, tetrahydrothiophenonyl, iminothiolane, dihydropyrrolyl, pyrrolidinyl, pyrrolidinonyl, imidazolidinonyl, imidazolidinethionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridinyl, piperidinyl, pentalactam, morpholinyl, pyrazoli(di)nyl, pyrimi(di)nyl, pyrazinyl, piperazinyl and azepinyl rings.

17. A compound according to claim 16, wherein $R_7$ represents a group Z, or a radical chosen from methyl, trifluoromethyl, ethyl, 2-chloroethyl, propyl, 3-chloropropyl, isopropyl, butyl, thiophen-2-yl, hydroxyl, ethoxy, amino and dimethylamino radicals.

18. A compound according to claim 17, wherein $R_7$ represents a group —D', —E—D' or —NH—E—D', in which —E— represents a —$(CH_2)_q$— arm, q is an integer equal to 1 or 2, and D' is chosen from 3-methylimidazolidinium-1-yl, 3-(2-hydroxyethyl) imidazolidinium-1-yl, 1,2,4-triazolinium-1-yl, 1,2,4-triazolinium-4-yl, N—($C_1$–$C_4$)alkylpyridinium-2-yl, N—($C_1$–$C_4$)alkylpyridinium-3-yl, N—($C_1$–$C_4$) alkylpyridinium-4-yl, N-(2-hydroxyethyl)-pyridinium-2-yl, N-(2-hydroxyethyl)pyridinium-3-yl, N-(2-hydroxyethyl) pyridinium-4-yl, pyridinium-1-yl, tri($C_1$–$C_4$ alkyl) ammonium-N-yl, 1-methylpiperidinium-1-yl and 1,4-dimethyipiperazinium-1-yl groups; or a methyl, ethyl or dimethylamino radical.

19. A compound according to claim 1, wherein Y represents a radical chosen from hydrogen, chlorine, fluorine and bromine atoms; methoxy, ethoxy, propoxy, benzyloxy and phenoxy groups; and —OCH₂CH₂OMe; —OCH₂CH₂OMe; —OCH₂CH₂NMe₂; —OCH₂(CO)OH, —OCH₂(CO)OMe, —OCH₂(CO)OEt, —SCH₂CH₂CO₂H and NHSO₂Me groups.

20. A compound according to claim 19, wherein Y represents a radical chosen from hydrogen, and chlorine atoms, and methoxy, —OCH₂(CO)OH and —OCH₂(CO)OMe groups.

21. compound according claim 1 wherein D is chosen from imidazolinium, thiazolinium, oxazolinium, pyrrolinium, 1,2,3-triazolinium, 1,2,4-triazolinium, isoxazolinium, isothiazolinium, imidazolidinium, thiazolidinium, pyrazolinium, pyrazolidinium, oxazolidinium, pyrazolotriazolinium, pyrazoloimidazolinium, pyrrolotriazolinium, pyrazolopyrimidinium, pyrazolopyridinium, pyridinium, pyrimidinium, pyrazinium, triazinium, benzoimidazolinium, benzoxazolinium, benzothiazolinium, indolinium, indolidinium, isoindolinium, indazolinium, benzotriazolinium, quinolinium, tetrahydroquinolinium, benzoimidazolidinium, benzopyrimidinium, tetra (C₁–C₄) alkylammonium, dialkylpiperidinium, dialkylpyrrolidinium, dialkylmorpholinium, dialkylthiomorpholinium, dialkylpiperazinium, azepinium and 1,4-diazabicyclo-[2.2.2]octanium groups.

22. A compound according to claim 21, wherein D is chosen from 3-methylimidazolidinium-1-yl, 3-(2-hydroxyethyl)imidazolidinium-1-yl, 1,2,4-triazolinium-1-yl, 1,2,4-triazolinium-4-yl, N—(C₁–C₄)alkylpyridinium-2-yl, N—(C₁–C₄) alkylpyridinium-3-yl, N—(C₁–C₄) alkylpyridinium-4-yl, N-(2-hydroxyethyl)pyridinium-2-yl, N-(2-hydroxyethyl)pyridinium-3-yl, N-(2-hydroxyethyl)-pyridinium-4-yl, pyridinium-1-yl, trialkyl(C₁–C₄) ammonium-N-yl, 1-methylpiperidinium-1-yl and 1,4-dimethylpiperazinium-1-yl groups.

23. A compound according to claim 1, wherein:
i)
the radical R₁ is chosen group (G5) chosen from acetylamino, methanesulphonylamino, amido and methylamido radicals, —NH—C(O)—CH2—D1, —NH—SO2—CH2—CH2—D1, and —(CO)—NH—CH2—CH2—D1 groups in which D1 is chosen from 3-methylimidazolidinium-1-yl, triazolinium-1-yl, pyridinium-1-yl and trimethylammonium-N-yl groups;
the radical R₂ is at the 5-position and is chosen from group (G6) chosen from amino, methylamino, acetylamino and methanesulphonyl amino radicals, —NH—[C(O)]ₘ—CH₂—D1 groups in which m represents 0 or 1, and —NH—SO₂—CH₂—CH₂—D1 groups;
the radical R₃ represents a hydrogen atom;
the radical Y represents a radical chosen from group (G7) chosen from a hydrogen atom, and chlorine and methoxy radicals; or
ii)
the radical R₁ is chosen from group (G5) as defined above;
the radical R₂ is situated at the 8-position and represents a radical chosen from the group (G6) as defined above;
the radical R₃ represents a hydrogen atom;
the radical Y represents a radical chosen from the group (G7) as defined above; or
iii)
the radical R₁ represents a radical chosen from the group (G5) as defined above;
the radicals R₂ and R₃ each represent a hydrogen atom;
the radical Y represents a radical chosen from the group (G7) as defined above.

24. A compound according to claim 1, wherein the compound is chosen from:

3-[(1-Hydroxynaphthalen-2-ylcarbamoyl)methyl]-1-methyl-3H-imidazol-1-ium chloride;
3-[(1-Hydroxy-5-(2-(3-methyl-1H-imidazol-3-ium-1-yl)acetyl)aminonaphthalen-2-ylcarbamoyl)methyl]-1-methyl-3H-imidazol-1-ium dichloride;
3-[(1-Hydroxy-8-(2-(3-methyl-1H-imidazol-3-ium-1-yl)acetyl)aminonaphthalen-2-ylcarbamoyl)methyl]-1-methyl-3H-imidazol-1-ium dichloride;
3-[(I-Hydroxy-5-aminonaphthalen-2-ylcarbamoyl)methyl]-1-methyl-3H-imidazol-I-ium chloride;
3-[(I-Hydroxy-5-acetylaminonaphthalen-2-ylcarbamoyl)methyl]-1-methyl-3H-imidazol-I-ium chloride; -3-[(I-Hydroxy-5-methoxycarbonylaminonaphthalen-2-ylcarbamoyl)methyl]-1-methyl-3H-imidazol-1-ium chloride;
3-[(I-Hydroxy-2-acetylaminonaphthalen-5-ylcarbamoyl)methyl]-1-methyl-3H-imidazol-1-ium chloride;
3-[(I-Hydroxy-2-methoxycarbonylaminonaphthalen-5-ylcarbamoyl)methyl]-1-methyl-3H-imidazol-1-ium chloride;
-3-[(I-Hydroxy-5-methanesulphonylaminonaphthalen-2-ylcarbamoyl)methyl]-1-methyl-3H-imidazol-1-ium chloride;
3-[(I-Hydroxy-8-aminonaphthalen-2-ylcarbamoyl)methyl]-1-methyl-3H-imidazol-1-ium chloride;
3-[(I-Hydroxy-8-acetylaminonaphthalen-2-ylcarbamoyl)methyl]-1-methyl-3H-imidazol-1-ium chloride;
3-[(I-Hydroxy-8-methoxycarbonylaminonaphthalen-2-ylcarbamoyl)methyl]-1-methyl-3H-imidazol-1-ium chloride;
3-[(I-Hydroxy-2-acetylaminonaphthalen-8-ylcarbamoyl)methyl]-1-methyl-3H-imidazol-1-ium chloride;
3-[(1-Hydroxy-2-methoxycarbonylaminonaphthalen-8-ylcarbamoyl)methyl]-1-methyl-3H-imidazol-1-ium chloride;
3-[(I-Hydroxy-8-methanesulphonylaminonaphthalen-2-ylcarbamoyl)methyl]-1-methyl-3H-imidazol-1-ium chloride;
1-[(I-Hydroxynaphthalen-2-ylcarbamoyl)methyl]pyridinium chloride;
1-[(I-Hydroxy-5-(2-(pyridinium-1-yl)acetyl)aminonaphthalen-2-ylcarbamoyl)methyl]pyridinium dichloride;
1-[(I-Hydroxy-8-(2-(pyridinium-1-yl)acetyl)aminonaphthalen-2-ylcarbamoyl)methyl]pyridinium dichloride;
1-[(I-Hydroxy-5-aminonaphthalen-2-ylcarbamoyl)methyl]pyridinium chloride;
1-[(I-Hydroxy-5-acetylaminonaphthalen-2-ylcarbamoyl)methyl]pyridinium chloride;
1-[(I-Hydroxy-5-methoxycarbonylaminonaphthalen-2-ylcarbamoyl)methyl]pyridinium chloride;
1-[(I-Hydroxy-2-acetylaminonaphthalen-5-ylcarbamoyl)methyl]pyridinium chloride;
1-[(I-Hydroxy-2-methoxycarbonylaminonaphthalen-5-ylcarbamoyl)methyl]pyridinium chloride;
1-[(I-Hydroxy-5-methanesulphonylaminonaphthalen-2-ylcarbamoyl)methyl]pyridinium chloride;
1-[(I-Hydroxy-8-aminonaphthalen-2-ylcarbamoyl)methyl]pyridinium chloride;
1-[(I-Hydroxy-8-acetylaminonaphthalen-2-ylcarbamoyl)methyl]pyridinium chloride;
1-[(I-Hydroxy-8-methoxycarbonylaminonaphthalen-2-ylcarbamoyl)methyl]pyridinium chloride;
1-[(I-Hydroxy-2-acetylaminonaphthalen-8-ylcarbamoyl)methyl]pyridinium chloride;

1-[(I-Hydroxy-2-methoxycarbonylaminonaphthalen-8-ylcarbamoyl)methyl]pyridinium chloride;
1-[(I-Hydroxy-8-methanesulphonylaminonaphthalen-2-ylcarbamoyl)methyl]pyridinium chloride;
1-[(I-Hydroxynaphthalen-2-ylcarbamoyl)methyl]-1,4-dimethylpiperazin-1-ium chloride;
1-[(I-Hydroxy-5-(2-(1,4-dimethylpiperazin-1-ium-1-yl)acetyl)aminonaphthalen-2-ylcarbamoyl)methyl]-1,4-dimethylpiperazin-1-ium dichloride;
1-[(I-Hydroxy-8-(2-(1,4-dimethylpiperazin-1-ium-1-yl)acetyl)aminonaphthalen-2-ylcarbamoyl)methyl]-1,4-dimethylpiperazin-1-ium dichloride;
1-[(I-Hydroxy-5-aminonaphthalen-2-ylcarbamoyl)methyl]-1,4-dimethylpiperazin-1-ium chloride;
1-[(I-Hydroxy-5-acetylaminonaphthalen-2-ylcarbamoyl)methyl]-1,4-dimethylpiperazin-1-ium chloride;
1-[(I-Hydroxy-5-methoxycarbonylaminonaphthalen-2-ylcarbamoyl)methyl]-1,4-dimethylpiperazin-1-ium chloride;
1-[(I-Hydroxy-2-acetylaminonaphthalen-5-ylcarbamoyl)methyl]-1,4-dimethylpiperazin-1-ium chloride;
1-[(I-Hydroxy-2-methoxycarbonylaminonaphthalen-5-ylcarbamoyl)methyl]-1,4-dimethylpiperazin-1-ium chloride;
1-[(I-Hydroxy-5-methanesulphonylaminonaphthalen-2-ylcarbamoyl)methyl]-1,4-dimethylpiperazin-1-ium chloride;
1-[(I-Hydroxy-8-aminonaphthalen-2-ylcarbamoyl)methyl]-1,4-dimethylpiperazin-1-ium chloride;
1-[(I-Hydroxy-8-acetylaminonaphthalen-2-ylcarbamoyl)methyl]-1,4-dimethylpiperazin-1-ium chloride;
1-[(I-Hydroxy-8-methoxycarbonylaminonaphthalen-2-ylcarbamoyl)methyl]-1,4-dimethylpiperazin-1-ium chloride;
1-[(I-Hydroxy-2-acetylaminonaphthalen-8-ylcarbamoyl)methyl]-1,4-dimethylpiperazin-1-ium chloride;
1-[(I-Hydroxy-2-methoxycarbonylaminonaphthalen-8-ylcarbamoyl)methyl]-1,4-dimethylpiperazin-1-ium chloride;
1-[(I-Hydroxy-8-methanesulphonylaminonaphthalen-2-ylcarbamoyl)methyl]-1,4-dimethylpiperazin-1-ium chloride; and acid addition salts thereof.

25. A compound according to any one of claims 1–24, wherein the acid addition salts are chosen from hydrochlorides, hydrobromides, sulphates, citrates, succinates, tartrates, lactates and acetates.

26. A method of dyeing of keratinous fibres, comprising dyeing the fibres with an oxidation base and an oxidation coupler, wherein the coupler is chosen from a compound of the following formula (I) or an acid addition salt thereof:

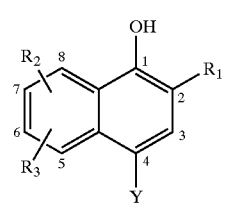

(I)

wherein:
R$_1$ represents a group chosen from —NR$_4$(C=O)R$_5$, —NR$_6$SO$_2$R$_7$ and —(C=O)NR$_6$R$_8$, the radicals R$_4$, R$_5$, R$_6$, R$_7$ and R$_8$ being as defined below;
R$_2$ and R$_3$, which are identical or different, represent a hydrogen atom; a halogen atom; a group Z as defined below; or a radical comprising from 1 to 20 carbon atoms, wherein the radical is linear or branched, wherein the branch(es) may form one or more carbon-containing rings comprising from 3 to 7 members, wherein the radical may contain bonds chosen from one or more double bonds and one or more triple bonds, wherein the double bonds may lead to aromatic groups, wherein one or more carbon atoms of the radical may be replaced with an oxygen, nitrogen or sulphur atom or with an SO$_2$ group, and in which the carbon atoms may, independently of each other, be substituted with one or more halogen atoms; it being understood that:
the said radicals R$_2$ and R$_3$ cannot be linked to the benzene ring of formula (I) by an —NH—NH— bond; and R$_2$ and R$_3$ do not contain a peroxide bond or diazo, nitro and nitroso radicals;
R$_2$ and R$_3$ cannot represent a hydroxyl radical or a thio radical;
R$_2$ and R$_3$ cannot each represent, simultaneously, an amino, alkylamino, acylamino or sulphonylamino radical;
Y represents a hydrogen or halogen atom; a group —OR$_9$, —SR$_9$, or —NH—SO$_2$R$_9$ in which R$_9$ represents a C$_1$–C$_6$ alkyl radical, linear or branched, wherein the branch(es) may form one or more rings comprising from 3 to 6 members, wherein the radical may unsubstituted or substituted with one or more radicals chosen from halogen atoms, hydroxyl radicals, and C$_1$–C$_4$ alkoxy, amino, and amino(C$_1$–C$_4$ alkyl) radicals; a phenyl radical, wherein the phenyl radical may be unsubstituted or substituted with one or two radicals chosen from C$_1$–C$_4$ alkyl, trifluoromethyl, carboxyl, C$_1$–C$_4$ alkoxycarbonyl, halogen, hydroxyl, C$_1$–C$_4$ alkoxy, amino, and amino(C$_1$–C$_4$ alkyl) radicals; or a benzyl radical;
R$_4$, R$_6$ and R$_8$, which are identical or different, represent a hydrogen atom; a group Z as defined below; or a radical comprising from 1 to 15 carbon atoms, linear or branched, wherein the branch(es) may form one or more carbon-containing rings comprising from 3 to 7 members, wherein the radical may contain bonds chosen from one or more double bonds and one or more triple bonds, wherein the double bonds may lead to aromatic groups, wherein one or more carbon atoms in the radical may be replaced with an oxygen, nitrogen, or sulphur atom or with an SO$_2$ group, and in which the carbon atoms may, independently of each other, be substituted with one or more halogen atoms;
it being understood that the SO$_2$ group is not directly linked to the nitrogen atom carrying the radical R$_4$ or R$_6$;
it being understood that the —(C=O)— group is not directly linked to the nitrogen atom carrying the radical R$_6$;
it being understood that the radicals R$_4$, R$_6$ and R$_8$ do not contain a peroxide bond or diazo, nitro and nitroso radicals;
it being understood that the radicals R$_4$, R$_6$ and R$_8$ cannot represent a hydroxyl radical, a thio radical, an amino radical, an alkoxy radical, or an alkylthio radical;
R$_5$ and R$_7$, which are identical or different, represent a hydrogen atom; a group Z as defined below; or a radical comprising from 1 to 20 carbon atoms, wherein the radical may be linear or branched, wherein the branch (es) may form one or more carbon-containing rings comprising from 3 to 7 members, wherein the radical may contain bond chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms;

it being understood that the said radicals $R_5$ and $R_7$ do not contain peroxide bonds or diazo, nitro and nitroso radicals;

it being understood that $R_5$ cannot represent a hydroxyl radical or a thio radical;

it being understood that $R_7$ cannot represent a thio radical;

it being understood that the radicals $R_4$ and $R_5$ on the one hand, and the radicals $R_6$ and $R_8$ on the other hand, can, in addition, be linked to form, independently of each other, a saturated or unsaturated ring comprising from 5 to 7 members, the members being chosen from carbon, nitrogen and acyl, each member being unsubstituted or substituted with 1 or 2 radicals R, which are identical or different, R being a $C_1$–$C_8$ alkyl radical, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms; the said ring containing no peroxide bonds or diazo, nitro and nitroso radicals;

Z is a cationic group represented by the following formula (II):

wherein:

n can take the value 0 or 1;

B an alkyl radical comprising from 1 to 15 carbon atoms, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, and wherein one or more carbon atoms in the radical may be replaced with an oxygen, nitrogen or sulphur atom or with an $-SO_2$ radical; and wherein one or more carbon atoms in the radical may, independently of each other, be substituted with one or more halogen atoms or with one or more groups Z; the said radical B containing no peroxide bond or diazo, nitro, or nitroso radicals;

D is chosen from the cationic groups of the following formulae (III) and (IV):

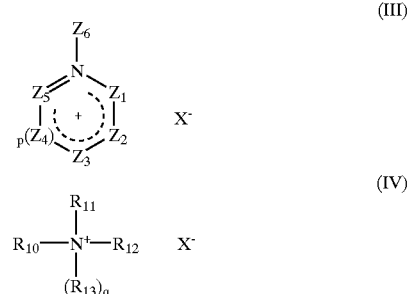

wherein:

p and q can, independently of each other, take the value 0 or 1;

the radical B is linked to the group D by any one of the atoms of the radical D;

when n=0 and q=0, then the group of formula (IV) can be linked to the compound of formula (I) directly by the nitrogen atom of the quaternary ammonium;

$Z_1$, $Z_2$, $Z_3$ and $Z_4$, independently of each other, represent an oxygen atom; a sulphur atom; a nitrogen atom which is unsubstituted or substituted with a radical $R_{14}$; or a carbon atom which is unsubstituted or substituted with one or two radicals $R_{14}$, which are identical or different;

$Z_5$ represents a nitrogen atom or a carbon atom which is unsubstituted or substituted with a radical $R_{14}$;

$Z_6$ can have the same meanings as those indicated below for the radical $R_{14}$; it being understood that $Z_6$ is different from a hydrogen atom;

the radicals $Z_1$ or $Z_5$ can, in addition, form with $Z_6$ a saturated or unsaturated ring comprising from 5 to 7 members, each member being unsubstituted or substituted with one or two radicals $R_{14}$ which are identical or different;

$R_{14}$ represents a hydrogen atom; a group Z; or a radical comprising from 1 to 10 carbon atoms, linear or branched, which may contain bonds chosen from one or more double bonds and one or more triple bonds, wherein the double bonds may lead to aromatic groups, wherein one or more carbon atoms of the radical may be replaced with an oxygen, nitrogen or sulphur atom, or with an $SO_2$ group, and wherein one or more carbon atoms of the radical may, independently of each other, be substituted with one or more halogen atoms; the said radical containing no peroxide bond or diazo, nitro and nitroso radicals;

it being possible, in addition, for two of the adjacent radicals $Z_1$, $Z_2$, $Z_3$, $Z_4$ and $Z_5$ to form a ring comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;

$R_{10}$, $R_{11}$, $R_{12}$ and $R_{13}$, which are identical or different, have the same meanings as those indicated above for the radical $R_{14}$;

it being possible for the radicals $R_{10}$, $R_{11}$, $R_{12}$ and $R_{13}$ to also form, in pairs with the quaternary nitrogen atom to which they are attached, one or more saturated rings comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;

$X^-$ represents an organic or inorganic anion;

with the proviso that at least one of the groups $R_1$ to $R_3$ represents or contains a group Z.

27. A composition for the oxidation dyeing of keratinous fibres, comprising, in a medium appropriate for dyeing:
   at least one oxidation base, and
   at least one coupler chosen from a compound of the following formula (I) or an acid addition salt thereof:

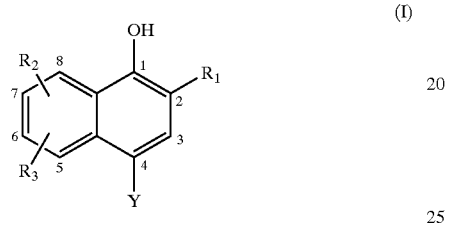

(I)

wherein:
$R_1$ represents a group chosen from $-NR_4(C=O)R_5$, $-NR_6SO_2R_7$ and $-(C=O)NR_6R_8$, the radicals $R_4$, $R_5$, $R_6$, $R_7$ and $R_8$ being as defined below;

$R_2$ and $R_3$, which are identical or different, represent a hydrogen atom; a halogen atom; a group Z as defined below; or a radical comprising from 1 to 20 carbon atoms, wherein the radical is linear or branched, wherein the branch(es) may form one or more carbon-containing rings comprising from 3 to 7 members, wherein the radical may contain bonds chosen from one or more double bonds and one or more triple, bonds, wherein the double bonds may lead to aromatic groups, wherein one or more carbon atoms of the radical may be replaced with an oxygen, nitrogen or sulphur atom or with an $SO_2$ group, and in which the carbon atoms may, independently of each other, be substituted with one or more halogen atoms; it being understood that:

the said radicals $R_2$ and $R_3$ cannot be linked to the benzene ring of formula (I) by an $-NH-NH-$ bond; and $R_2$ and $R_3$ do not contain a peroxide bond or diazo, nitro and nitroso radicals;

$R_2$ and $R_3$ cannot represent a hydroxyl radical or a thio radical;

$R_2$ and $R_3$ cannot each represent, simultaneously, an amino, alkylamino, acylamino or sulphonylamino radical;

Y represents a hydrogen or halogen atom; a group $-OR_9$, $-SR_9$, or $-NH-SO_2R_9$ in which $R_9$ represents a $C_1-C_6$ alkyl radical, linear or branched, wherein the branch(es) may form one or more rings comprising from 3 to 6 members, wherein the radical may unsubstituted or substituted with one or more radicals chosen from halogen atoms, hydroxyl radicals, and $C_1-C_4$ alkoxy, amino, and amino ($C_1-C_4$ alkyl) radicals; a phenyl radical, wherein the phenyl radical may be unsubstituted or substituted with one or two radicals chosen from $C_1-C_4$ alkyl, trifluoromethyl, carboxyl, $C_1-C_4$ alkoxycarbonyl, halogen, hydroxyl, $C_1-C_4$ alkoxy, amino, and amino ($C_1-C_4$ alkyl) radicals; or a benzyl radical;

$R_4$, $R_6$ and $R_8$, which are identical or different, represent a hydrogen atom; a group Z as defined below; or a radical comprising from 1 to 15 carbon atoms, linear or branched, wherein the branch(es) may form one or more carbon-containing rings comprising from 3 to 7 members, wherein the radical may contain bonds chosen from one or more double bonds and one or more triple bonds, wherein the double bonds may lead to aromatic groups, wherein one or more carbon atoms in the radical may be replaced with an oxygen, nitrogen, or sulphur atom or with an $SO_2$ group, and in which the carbon atoms may, independently of each other, be substituted with one or more halogen atoms;

it being understood that the $SO_2$ group is not directly linked to the nitrogen atom carrying the radical $R_4$ or $R_6$;

it being understood that the $-(C=O)-$ group is not directly linked to the nitrogen atom carrying the radical $R_6$;

it being understood that the radicals $R_4$, $R_6$ and $R_8$ do not contain a peroxide bond or diazo, nitro and nitroso radicals;

it being understood that the radicals $R_4$, $R_6$ and $R_8$ cannot represent a hydroxyl radical, a thio radical, an amino radical, an alkoxy radical, or an alkylthio radical;

$R_5$ and $R_7$, which are identical or different, represent a hydrogen atom; a group Z as defined below; or a radical comprising from 1 to 20 carbon atoms, wherein the radical may be linear or branched, wherein the branch(es) may form one or more carbon-containing rings comprising from 3 to 7 members, wherein the radical may contain bond chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms;

it being understood that the said radicals $R_5$ and $R_7$ do not contain peroxide bonds or diazo, nitro and nitroso radicals;

it being understood that $R_5$ cannot represent a hydroxyl radical or a thio radical;

it being understood that $R_7$ cannot represent a thio radical;

it being understood that the radicals $R_4$ and $R_5$ on the one hand, and the radicals $R_6$ and $R_8$ on the other hand, can, in addition, be linked to form, independently of each other, a saturated or unsaturated ring comprising from 5 to 7 members, the members being chosen from carbon, nitrogen and acyl, each member being unsubstituted or substituted with 1 or 2 radicals R, which are identical or different, R being a $C_1-C_8$ alkyl radical, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms; the said ring containing no peroxide bonds or diazo, nitro and nitroso radicals;

Z is a cationic group represented by the following formula (II):

wherein:

n can take the value 0 or 1;

B represents an alkyl radical comprising from 1 to 15 carbon atoms, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, and wherein one or more carbon atoms in the radical may be replaced with an oxygen, nitrogen or sulphur atom or with an —$SO_2$ radical; and wherein one or more carbon atoms in the radical may, independently of each other, be substituted with one or more halogen atoms or with one or more groups Z; the said radical B containing no peroxide bond or diazo, nitro, or nitroso radicals;

D is chosen from the cationic groups of the following formulae (III) and (IV):

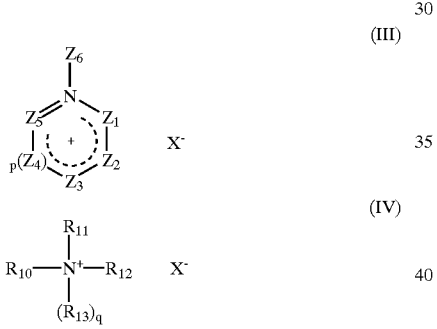

wherein:

p and q can, independently of each other, take the value 0 or 1;

the radical B is linked to the group D by any one of the atoms of the radical D;

when n=0 and q=0, then the group of formula (IV) can be linked to the compound of formula (I) directly by the nitrogen atom of the quaternary ammonium;

$Z_1$, $Z_2$, $Z_3$ and $Z_4$, independently of each other, represent an oxygen atom; a sulphur atom; a nitrogen atom which is unsubstituted or substituted with a radical $R_{14}$; or a carbon atom which is unsubstituted or substituted with one or two radicals $R_{14}$, which are identical or different;

$Z_5$ represents a nitrogen atom or a carbon atom which is unsubstituted or substituted with a radical $R_{14}$;

$Z_6$ can have the same meanings as those indicated below for the radical $R_{14}$; it being understood that $Z_6$ is different from a hydrogen atom;

the radicals $Z_1$ or $Z_5$ can, in addition, form with $Z_6$ a saturated or unsaturated ring comprising from 5 to 7 members, each member being unsubstituted or substituted with one or two radicals $R_{14}$ which are identical or different;

$R_{14}$ represents a hydrogen atom; a group Z; or a radical comprising from 1 to 10 carbon atoms, linear or branched, which may contain bonds chosen from one or more double bonds and one or more triple bonds, wherein the double bonds may lead to aromatic groups, wherein one or more carbon atoms of the radical may be replaced with an oxygen, nitrogen or sulphur atom, or with an $SO_2$ group, and wherein one or more carbon atoms of the radical may, independently of each other, be substituted with one or more halogen atoms; the said radical containing no peroxide bond or diazo, nitro and nitroso radicals; q it being possible, in addition, for two of the adjacent radicals $Z_1$, $Z_2$, $Z_3$, $Z_4$ and $Z_5$ to form a ring comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;

$R_{10}$, $R_{11}$, $R_{12}$ and $R_{13}$, which are identical or different, have the same meanings as those indicated above for the radical $R_{14}$;

it being possible for the radicals $R_{10}$, $R_{11}$, $R_{12}$ and $R_{13}$ to also form, in pairs with the quaternary nitrogen atom to which they are attached, one or more saturated rings comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;

$X^-$ represents an organic or inorganic anion;

with the proviso that at least one of the groups $R_1$ to $R_3$ represents or contains a group Z.

28. A composition according to claim 27, wherein the composition comprises the compound of formula (I) or an acid addition salt thereof in an amount ranging from 0.0005 to 12% by weight of the total weight of the dyeing composition.

29. A composition according to claim 27, wherein the at least one oxidation base is chosen from para-phenylenediamines, bisphenylalkylenediamines, para-aminophenols, ortho-aminophenols and heterocyclic bases, and acid addition salts thereof.

30. A composition according to claim 27, wherein the composition comprises the at least one oxidation base in an amount ranging from 0.0005 to 12% by weight of the total weight of the dyeing composition.

31. A composition according to claim 27, comprising, in addition to the compound according to claim 1, at least one of (1) at least one additional coupler chosen from meta-phenylenediamines, meta-aminophenols, meta-diphenols and heterocyclic couplers, and acid addition salts thereof, and (2) at least one direct dye.

32. A composition according to claim 31, the at least one additional coupler is present in an amount ranging from 0.0001 to 10% by weight of the total weight of the dyeing composition.

33. A composition according to any one of claims 27 to 32, wherein the acid addition salts are chosen from hydrochlorides, hydrobromides, sulphates, citrates, succinates, tartrates, lactates and acetates.

34. A method of oxidation dyeing of keratinous fibres, comprising:

applying to the fibers at least one dyeing composition; and developing a color at a pH chosen from acidic, neutral and alkaline pH with the aid of an oxidizing agent which is added just at the time of use to the dyeing composition and which is present in an oxidizing composition applied at least one of simultaneously and sequentially in a separate manner, wherein the at least one dyeing composition comprises in a medium appropriate for dyeing:
at least one oxidation base, and
at least one coupler chosen from a compound of the following formula (I) or an acid addition salt thereof:

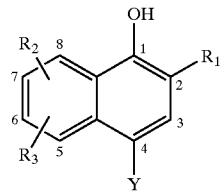

(I)

wherein:
$R_1$ represents a group chosen from —$NR_4(C=O)R_5$, —$NR_6SO_2R_7$ and —$(C=O)NR_6R_8$, the radicals $R_4$, $R_5$, $R_6$, $R_7$ and $R_8$ being as defined below;

$R_2$ and $R_3$, which are identical or different, represent a hydrogen atom; a halogen atom; a group Z as defined below; or a radical comprising from 1 to 20 carbon atoms, wherein the radical is linear or branched, wherein the branch(es) may form one or more carbon-containing rings comprising from 3 to 7 members, wherein the radical may contain bonds chosen from one or more double bonds and one or more triple bonds, wherein the double bonds may lead to aromatic groups, wherein one or more carbon atoms of the radical may be replaced with an oxygen, nitrogen or sulphur atom or with an $SO_2$ group, and in which the carbon atoms may, independently of each other, be substituted with one or more halogen atoms; it being understood that:

the said radicals $R_2$ and $R_3$ cannot be linked to the benzene ring of formula (I) by an —NH—NH— bond; and $R_2$ and $R_3$ do not contain a peroxide bond or diazo, nitro and nitroso radicals;

$R_2$ and $R_3$ cannot represent a hydroxyl radical or a thio radical;

$R_2$ and $R_3$ cannot each represent, simultaneously, an amino, alkylamino, acylamino or sulphonylamino radical;

Y represents a hydrogen or halogen atom; a group —$OR_9$, —$SR_9$, or —NH—$SO_2R_9$ in which $R_9$ represents a $C_1$–$C_6$ alkyl radical, linear or branched, wherein the branch(es) may form one or more rings comprising from 3 to 6 members, wherein the radical may unsubstituted or substituted with one or more radicals chosen from halogen atoms, hydroxyl radicals, and $C_1$–$C_4$ alkoxy, amino, and amino($C_1$–$C_4$ alkyl) radicals; a phenyl radical, wherein the phenyl radical may be unsubstituted or substituted with one or two radicals chosen from $C_1$–$C_4$ alkyl, trifluoromethyl, carboxyl, $C_1$–$C_4$ alkoxycarbonyl, halogen, hydroxyl, $C_1$–$C_4$ alkoxy, amino, and amino($C_1$–$C_4$ alkyl) radicals; or a benzyl radical;

$R_4$, $R_6$ and $R_8$, which are identical or different, represent a hydrogen atom; a group Z as defined below; or a radical comprising from 1 to 15 carbon atoms, linear or branched, wherein the branch(es) may form one or more carbon-containing rings comprising from 3 to 7 members, wherein the radical may contain bonds chosen from one or more double bonds and one or more triple bonds, wherein the double bonds may lead to aromatic groups, wherein one or more carbon atoms in the radical may be replaced with an oxygen, nitrogen, or sulphur atom or with an $SO_2$ group, and in which the carbon atoms may, independently of each other, be substituted with one or more halogen atoms;

it being understood that the $SO_2$ group is not directly linked to the nitrogen atom carrying the radical $R_4$ or $R_6$;

it being understood that the —(C=O)— group is not directly linked to the nitrogen atom carrying the radical $R_6$;

it being understood that the radicals $R_4$, $R_6$ and $R_8$ do not contain a peroxide bond or diazo, nitro and nitroso radicals;

it being understood that the radicals $R_4$, $R_6$ and $R_8$ cannot represent a hydroxyl radical, a thio radical, an amino radical, an alkoxy radical, or an alkylthio radical;

$R_5$ and $R_7$, which are identical or different, represent a hydrogen atom; a group Z as defined below; or a radical comprising from 1 to 20 carbon atoms, wherein the radical may be linear or branched, wherein the branch(es) may form one or more carbon-containing rings comprising from 3 to 7 members, wherein the radical may contain bond chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms;

it being understood that the said radicals $R_5$ and $R_7$ do not contain peroxide bonds or diazo, nitro and nitroso radicals;

it being understood that $R_5$ cannot represent a hydroxyl radical or a thio radical;

it being understood that $R_7$ cannot represent a thio radical;

it being understood that the radicals $R_4$ and $R_5$ on the one hand, and the radicals $R_6$ and $R_8$ on the other hand, can, in addition, be linked to form, independently of each other, a saturated or unsaturated ring comprising from 5 to 7 members, the members being chosen from carbon, nitrogen and acyl, each member being unsubstituted or substituted with 1 or 2 radicals R, which are identical or different, R being a $C_1$–$C_8$ alkyl radical, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms; the said ring containing no peroxide bonds or diazo, nitro and nitroso radicals;

Z is a cationic group represented by the following formula (II):

(II)

wherein:
n can take the value 0 or 1;
B represents an alkyl radical comprising from 1 to 15 carbon atoms, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, and wherein one or more carbon atoms in the radical may be replaced with an oxygen, nitrogen or sulphur atom or with an $-SO_2$ radical; and wherein one or more carbon atoms in the radical may, independently of each other, be substituted with one or more halogen atoms or with one or more groups Z; the said radical B containing no peroxide bond or diazo, nitro, or nitroso radicals;

D is chosen from the cationic groups of the following formulae (III) and (IV):

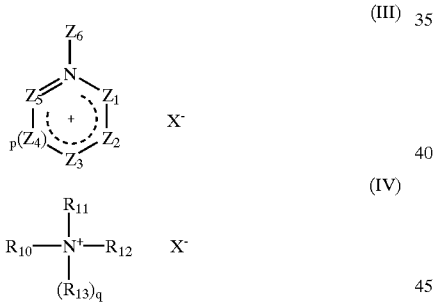

wherein
p and q can, independently of each other, take the value 0 or 1;
the radical B is linked to the group D by any one of the atoms of the radical D;
when n=0 and q=0, then the group of formula (IV) can be linked to the compound of formula (I) directly by the nitrogen atom of the quaternary ammonium;
$Z_1$, $Z_2$, $Z_3$ and $Z_4$, independently of each other, represent an oxygen atom; a sulphur atom; a nitrogen atom which is unsubstituted or substituted with a radical $R_{14}$; or a carbon atom which is unsubstituted or substituted with one or two radicals $R_{14}$, which are identical or different;
$Z_5$ represents a nitrogen atom or a carbon atom which is unsubstituted or substituted with a radical $R_{14}$;
$Z_6$ can have the same meanings as those indicated below for the radical $R_{14}$; it being understood that $Z_6$ is different from a hydrogen atom;

the radicals $Z_1$ or $Z_5$ can, in addition, form with $Z_6$ a saturated or unsaturated ring comprising from 5 to 7 members, each member being unsubstituted or substituted with one or two radicals $R_{14}$ which are identical or different;

$R_{14}$ represents a hydrogen atom; a group Z; or a radical comprising from 1 to 10 carbon atoms, linear or branched, which may contain bonds chosen from one or more double bonds and one or more triple bonds, wherein the double bonds may lead to aromatic groups, wherein one or more carbon atoms of the radical may be replaced with an oxygen, nitrogen or sulphur atom, or with an $SO_2$ group, and wherein one or more carbon atoms of the radical may, independently of each other, be substituted with one or more halogen atoms; the said radical containing no peroxide bond or diazo, nitro and nitroso radicals;

it being possible, in addition, for two of the adjacent radicals $Z_1$, $Z_2$, $Z_3$, $Z_4$ and $Z_5$ to form a ring comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;

$R_{10}$, $R_{11}$, $R_{12}$ and $R_{13}$, which are identical or different, have the same meanings as those indicated above for the radical $R_{14}$;

it being possible for the radicals $R_{10}$, $R_{11}$, $R_{12}$ and $R_{13}$ to also form, in pairs with the quaternary nitrogen atom to which they are attached, one or more saturated rings comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;

$X^-$ represents an organic or inorganic anion;

with the proviso that at least one of the groups $R_1$ to $R_3$ represents or contains a group Z.

35. A method according to claim 34, wherein the oxidizing agent is chosen from hydrogen peroxide, urea peroxide, alkali metal bromates, persalts and enzymes.

36. A multicompartment device or multicompartment dyeing "kit", comprising a first compartment and a second compartment, wherein the first compartment comprises at least one dyeing composition, and the second compartment comprises an oxidizing composition, wherein the dyeing composition comprises in a medium appropriate for dyeing:
at least one oxidation base, and
at least one coupler chosen from a compound of the following formula (I) or an acid addition salt thereof:

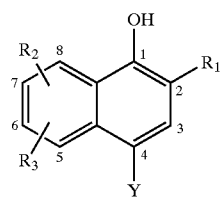

(I)

wherein:
$R_1$ represents a group chosen from —$NR_4$(C=O)$R_5$, —$NR_6SO_2R_7$ and —(C=O)$NR_6R_8$, the radicals $R_4$, $R_5$, $R_6$, $R_7$ and $R_8$ being as defined below;

$R_2$ and $R_3$, which are identical or different, represent a hydrogen atom; a halogen atom; a group Z as defined below; or a radical comprising from 1 to 20 carbon atoms, wherein the radical is linear or branched, wherein the branch(es) may form one or more carbon-containing rings comprising from 3 to 7 members, wherein the radical may contain bonds chosen from one or more double bonds and one or more triple bonds, wherein the double bonds may lead to aromatic groups, wherein one or more carbon atoms of the radical may be replaced with an oxygen, nitrogen or sulphur atom or with an $SO_2$ group, and in which the carbon atoms may, independently of each other, be substituted with one or more halogen atoms; it being understood that:
  the said radicals $R_2$ and $R_3$ cannot be linked to the benzene ring of formula (I) by an —NH—NH— bond; and $R_2$ and $R_3$ do not contain a peroxide bond or diazo, nitro and nitroso radicals;

$R_2$ and $R_3$ cannot represent a hydroxyl radical or a thio radical;

$R_2$ and $R_3$ cannot each represent, simultaneously, an amino, alkylamino, acylamino or sulphonylamino radical;

Y represents a hydrogen or halogen atom; a group —$OR_9$, —$SR_9$, or —NH—$SO_2R_9$ in which $R_9$ represents a $C_1$–$C_6$ alkyl radical, linear or branched, wherein the branch(es) may form one or more rings comprising from 3 to 6 members, wherein the radical may unsubstituted or substituted with one or more radicals chosen from halogen atoms, hydroxyl radicals, and $C_1$–$C_4$ alkoxy, amino, and amino($C_1$–$C_4$ alkyl) radicals; a phenyl radical, wherein the phenyl radical may be unsubstituted or substituted with one or two radicals chosen from $C_1$–$C_4$ alkyl, trifluoromethyl, carboxyl, $C_1$–$C_4$ alkoxycarbonyl, halogen, hydroxyl, $C_1$–$C_4$ alkoxy, amino, and amino ($C_1$–$C_4$ alkyl) radicals; or a benzyl radical;

$R_4$, $R_6$ and $R_8$, which are identical or different, represent a hydrogen atom; a group Z as defined below; or a radical comprising from 1 to 15 carbon atoms, linear or branched, wherein the branch(es) may form one or more carbon-containing rings comprising from 3 to 7 members, wherein the radical may contain bonds chosen from one or more double bonds and one or more triple bonds, wherein the double bonds may lead to aromatic groups, wherein one or more carbon atoms in the radical may be replaced with an oxygen, nitrogen, or sulphur atom or with an $SO_2$ group, and in which the carbon atoms may, independently of each other, be substituted with one or more halogen atoms;

it being understood that the $SO_2$ group is not directly linked to the nitrogen atom carrying the radical $R_4$ or $R_6$;

it being understood that the —(C=O)— group is not directly linked to the nitrogen atom carrying the radical $R_6$;

it being understood that the radicals $R_4$, $R_6$ and $R_8$ do not contain a peroxide bond or diazo, nitro and nitroso radicals;

it being understood that the radicals $R_4$, $R_6$ and $R_8$ cannot represent a hydroxyl radical, a thio radical, an amino radical, an alkoxy radical, or an alkylthio radical;

$R_5$ and $R_7$, which are identical or different, represent a hydrogen atom; a group Z as defined below; or a radical comprising from 1 to 20 carbon atoms, wherein the radical may be linear or branched, wherein the branch(es) may form one or more carbon-containing rings comprising from 3 to 7 members, wherein the radical may contain bond chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms;

it being understood that the said radicals $R_5$ and $R_7$ do not contain peroxide bonds or diazo, nitro and nitroso radicals;

it being understood that $R_5$ cannot represent a hydroxyl radical or a thio radical;

it being understood that $R_7$ cannot represent a thio radical;

it being understood that the radicals $R_4$ and $R_5$ on the one hand, and the radicals $R_6$ and $R_8$ on the other hand, can, in addition, be linked to form, independently of each other, a saturated or unsaturated ring comprising from 5 to 7 members, the members being chosen from carbon, nitrogen and acyl, each member being unsubstituted or substituted with 1 or 2 radicals R, which are identical or different, R being a $C_1$–$C_8$ alkyl radical, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, wherein one or more carbon atoms of the radical may be replaced with an oxygen, nitrogen, or sulphur atom or with an $SO_2$ group, and wherein the carbon atoms of the radical may, independently of each other, be substituted with one or more halogen atoms; the said ring containing no peroxide bonds or diazo, nitro and nitroso radicals;

Z is a cationic group represented by the following formula (II):

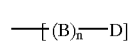
(II)

wherein:
n can take the value 0 or 1;
B represents an alkyl radical comprising from 1 to 15 carbon atoms, wherein the radical may be linear or branched, wherein the branch(es) may form one or more rings comprising from 3 to 7 members, wherein the radical may contain bonds chosen from one or more double bonds and one or more triple bonds, wherein the double bonds may lead to aromatic groups, and wherein one or more carbon atoms in the radical may be replaced with an oxygen, nitrogen or sulphur atom or with an —$SO_2$ radical; and wherein one or more carbon atoms in the radical may, independently of each other, be substituted with one or more halogen atoms or with one or more groups Z; the said radical B containing no peroxide bond or diazo, nitro, or nitroso radicals;
D is chosen from the cationic groups of the following formulae (III) and (IV):

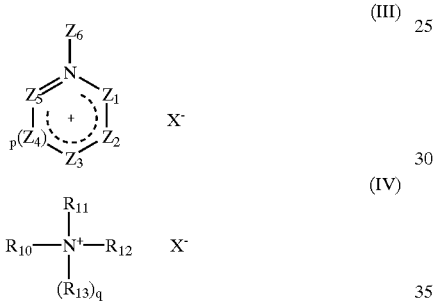

wherein:
p and q can, independently of each other, take the value 0 or 1;
the radical B is linked to the group D by any one of the atoms of the radical D;
when n=0 and q=0, then the group of formula (IV) can be linked to the compound of formula (I) directly by the nitrogen atom of the quaternary ammonium;
$Z_1$, $Z_2$, $Z_3$ and $Z_4$, independently of each other, represent an oxygen atom; a sulphur atom; a nitrogen atom which is unsubstituted or substituted with a radical $R_{14}$; or a carbon atom which is unsubstituted or substituted with one or two radicals $R_{14}$, which are identical or different;
$Z_5$ represents a nitrogen atom or a carbon atom which is unsubstituted or substituted with a radical $R_{14}$;

$Z_6$ can have the same meanings as those indicated below for the radical $R_{14}$; it being understood that $Z_6$ is different from a hydrogen atom;
the radicals $Z_1$ or $Z_5$ can, in addition, form with $Z_6$ a saturated or unsaturated ring comprising from 5 to 7 members, each member being unsubstituted or substituted with one or two radicals $R_{14}$ which are identical or different;
$R_{14}$ represents a hydrogen atom; a group Z; or a radical comprising from 1 to 10 carbon atoms, linear or branched, which may contain bonds chosen from one or more double bonds and one or more triple bonds, wherein the double bonds may lead to aromatic groups, wherein one or more carbon atoms of the radical may be replaced with an oxygen, nitrogen or sulphur atom, or with an $SO_2$ group, and wherein one or more carbon atoms of the radical may, independently of each other, be substituted with one or more halogen atoms; the said radical containing no peroxide bond or diazo, nitro and nitroso radicals;
it being possible, in addition, for two of the adjacent radicals $Z_1$, $Z_2$, $Z_3$, $Z_4$ and $Z_5$ to form a ring comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;
$R_{10}$, $R_{11}$, $R_{12}$ and $R_{13}$, which are identical or different, have the same meanings as those indicated above for the radical $R_{14}$;
it being possible for the radicals $R_{10}$, $R_{11}$, $R_{12}$ and $R_{13}$ to also form, in pairs with the quaternary nitrogen atom to which they are attached, one or more saturated rings comprising from 5 to 7 members, each member being independently represented by a carbon atom which is unsubstituted or substituted with one or two radicals $R_{14}$ which are identical or different; a nitrogen atom which is unsubstituted or substituted with a radical $R_{14}$; an oxygen atom; or a sulphur atom;
$X^-$ represents an organic or inorganic anion;
with the proviso that at least one of the groups $R_1$ to $R_3$ represents or contains a group Z.

* * * * *

UNITED STATES PATENT AND TRADEMARK OFFICE
CERTIFICATE OF CORRECTION

PATENT NO. : 6,605,124 B1
DATED : August 12, 2003
INVENTOR(S) : Jean-Jacques Vandenbossche et al.

It is certified that error appears in the above-identified patent and that said Letters Patent is hereby corrected as shown below:

Column 20,
Line 22, "thereof;" should read -- thereof: --.

Column 21,
Lines 57-58, "branch (es)" should read -- branch(es) --.

Column 24,
Line 5, "methylphenyl;" should read -- methylphenyl, --.

Column 25,
Line 2, "1,4-dimethyipiperazinium-1-yl" should read
-- 1,4-dimethylpiperazinium-1-yl --.

Column 27,
Lines 18-19, "1,4-dimethyipiperazinium-1-yl" should read
-- 1,4-dimethylpiperazinium-1-yl --.

Column 28,
Line 31, "according claim" should read -- according to claim --.

Column 29,
Line 37, "-(CH$_2$)$_q$-arm" should read -- -(CH$_2$)$_q$- arm --.
Lines 44-45, "1,4-dimethyipiperazinium-1-yl" should read
-- 1,4-dimethylpiperazinium-1-yl --.

Column 30,
Lines 62-63, "1,4-dimethyipiperazinium-1-yl" should read
-- 1,4-dimethylpiperazinium-1-yl --.

Column 31,
Line 8, "compound according claim 1" should read
-- A compound according to claim 1, --.

Column 32,
Lines 11-12, "3-[(I-Hydroxy-5-aminonaphthalen-2-ylcarbamoyl)methyl]-
1-methyl-3H-imidazol-I-ium chloride;" should read
-- 3-[(1-Hydroxy-5-aminonaphthalen-2-ylcarbamoyl)
methyl]-1-methyl-3H-imidazol-1-ium chloride --.

UNITED STATES PATENT AND TRADEMARK OFFICE
CERTIFICATE OF CORRECTION

PATENT NO.     : 6,605,124 B1
DATED          : August 12, 2003
INVENTOR(S)    : Jean-Jacques Vandenbossche et al.

It is certified that error appears in the above-identified patent and that said Letters Patent is hereby corrected as shown below:

Column 32 cont'd,
Lines 13-14, "3-[(I-Hydroxy-5-acetylaminonaphthalen-2-ylcarbamoyl)methyl]-1-methyl-3H-imidazol-I-ium chloride; -3-[I-" should read -- 3-[(1-Hydroxy-5-acetylaminonaphthalen-2-ylcarbamoyl)methyl]-1-methyl-3H-imidazol-1-ium chloride; 3-[(1- --.
Line 18, "3-[(I-Hydroxy-2-acetylaminonaphthalen-5-ylcarbamoyl)" should read -- 3-[(1-Hydroxy-2-acetylaminonaphthalen-5-ylcarbamoyl) --.
Line 20, " 3-[(I-Hydroxy-2-methoxycarbonylaminonaphthalen-5-" should read -- 3-[(1-Hydroxy-2-methoxycarbonylaminonaphthalen-5- --.
Line 23, "-3-[(I-Hydroxy-5-methanesulphonylaminonaphthalen-2-" should read -- 3-[(1-Hydroxy-5-methanesulphonylaminonaphthalen-2- --.
Line 26, "3-[(I-Hydroxy-8-aminonaphthalen-2-ylcarbamoyl)methyl]-" should read --3-[(1-Hydroxy-8-aminonaphthalen-2-ylcarbamoyl)methyl]- --.
Line 28, "3-[(I-Hydroxy-8-acetylaminonaphthalen-2-ylcarbamoyl)" should read -- 3-[(1-Hydroxy-8-acetylaminonaphthalen-2-ylcarbamoyl) --.
Line 30, "3-[(I-Hydroxy-8-methoxycarbonylaminonaphthalen-2-" should read -- 3-[(1-Hydroxy-8-methoxycarbonylaminonaphthalen-2- --.
Line 33, "3-[(I-Hydroxy-2-acetylaminonaphthalen-8-ylcarbamoyl)" should read -- 3-[(1-Hydroxy-2-acetylaminonaphthalen-8-ylcarbamoyl) --.
Line 37, "3-[(I-Hydroxy-8-methanesulphonylaminonaphthalen-2-" should read -- 3-[(1-Hydroxy-8-methanesulphonylaminonaphthalen-2- --.
Line 40, "1-[(I-Hydroxynaphthalen-2-ylcarbamoyl)methyl]" should read -- 1-[(1-Hydroxynaphthalen-2-ylcarbamoyl)methyl] --.
Line 42, "1-[(I-Hydroxy-5-(2-(pyridinium-1-yl)acetyl)" should read -- 1-[(1-Hydroxy-5-(2-(pyridinium-1-yl)acetyl) --.
Line 45, "1-[(I-Hydroxy-8-(2-(pyridinium-1-yl)acetyl)" should read -- 1-[(1-Hydroxy-8-(2-(pyridinium-1-yl)acetyl) --.
Line 48, "1-[(I-Hydroxy-5-aminonaphthalen-2-ylcarbamoyl)methyl]" should read -- 1-[(1-Hydroxy-5-aminonaphthalen-2-ylcarbamoyl)methyl] --.
Line 50, "1-[(I-Hydroxy-5-acetylaminonaphthalen-2-ylcarbamoyl)" should read -- 1-[(1-Hydroxy-5-acetylaminonaphthalen-2-ylcarbamoyl) --.

UNITED STATES PATENT AND TRADEMARK OFFICE
CERTIFICATE OF CORRECTION

PATENT NO.    : 6,605,124 B1
DATED         : August 12, 2003
INVENTOR(S)   : Jean-Jacques Vandenbossche et al.

It is certified that error appears in the above-identified patent and that said Letters Patent is hereby corrected as shown below:

Column 32 cont'd,
Line 52, "1-[(I-Hydroxy-5-methoxycarbonylaminonaphthalen-2-" should
read -- 1-[(1-Hydroxy-5-methoxycarbonylaminonaphthalen-2- --.
Line 54, "1-[(I-Hydroxy-2-acetylaminonaphthalen-5-ylcarbamoyl)" should
read -- 1-[(1-Hydroxy-2-acetylaminonaphthalen-5-ylcarbamoyl) --.
Line 56, "1-[(I-Hydroxy-2-methoxycarbonylaminonaphthalen-5-" should
read -- 1-[(1-Hydroxy-2-methoxycarbonylaminonaphthalen-5- --.
Line 58, "1-[(I-Hydroxy-5-methanesulphonylaminonaphthalen-2-" should
read -- 1-[(1-Hydroxy-5-methanesulphonylaminonaphthalen-2- --.
Line 60, "1-[(I-Hydroxy-8-aminonaphthalen-2-ylcarbamoyl)methyl]" should
read -- 1-[(1-Hydroxy-8-aminonaphthalen-2-ylcarbamoyl)methyl] --.
Line 62, "1-[(I-Hydroxy-8-acetylaminonaphthalen-2-ylcarbamoyl)" should
read -- 1-[(1-Hydroxy-8-acetylaminonaphthalen-2-ylcarbamoyl) --.
Line 64, "1-[(I-Hydroxy-8-methoxycarbonylaminonaphthalen-2-" should
read -- 1-[(1-Hydroxy-8-methoxycarbonylaminonaphthalen-2- --.
Line 66, "1-[(I-Hydroxy-2-acetylaminonaphthalen-8-ylcarbamoyl)" should
read -- 1-[(1-Hydroxy-2-acetylaminonaphthalen-8-ylcarbamoyl) --.

Column 33,
Line 1, "1-[(I-Hydroxy-2-methoxycarbonylaminonaphthalen-8-" should read
-- 1-[(1-Hydroxy-2-methoxycarbonylaminonaphthalen-8- --.
Line 3, "1-[(I-Hydroxy-8-methanesulphonylaminonaphthlen-2-" should read
-- 1-[(1-Hydroxy-8-methanesulphonylaminonaphthalen-2- --.
Line 5, "1-[(I-Hydroxynaphthalen-2-ylcarbamoyl)methyl]-1,4-" should
read -- 1-[(1-Hydroxynaphthalen-2-ylcarbamoyl)methyl]-1,4- --.
Line 7, "1-[(I-Hydroxy-5-(2-(1,4-dimethylpiperazin-1-ium-1-yl)" should
read -- 1-[(1-Hydroxy-5-(2-(1,4-dimethylpiperazin-1-ium-1-yl) --.
Line 10, "1-[(I-Hydroxy-8-(2-(1,4-dimethylpiperazin-1-ium-1-yl)" should
read -- 1-[(1-Hydroxy-8-(2-(1,4-dimethylpiperazin-1-ium-1-yl) --.
Line 13, "1-[(I-Hydroxy-5-aminonaphthalen-2-ylcarbamoyl)" should read
-- 1-[(1-Hydroxy-5-aminonaphthalen-2-ylcarbamoyl) --.
Line 14, "1-[(I-Hydroxy-5-acetylaminonaphthalen-2-" should read
-- 1-[(1-Hydroxy-5-acetylaminonaphthalen-2- --.

UNITED STATES PATENT AND TRADEMARK OFFICE
CERTIFICATE OF CORRECTION

PATENT NO. : 6,605,124 B1
DATED : August 12, 2003
INVENTOR(S) : Jean-Jacques Vandenbossche et al.

It is certified that error appears in the above-identified patent and that said Letters Patent is hereby corrected as shown below:

Column 33 cont'd,
Line 16, "1-[(I-Hydroxy-5-methoxycarbonylaminonaphthalen-2-" should
read -- 1-[(I-Hydroxy-5-methoxycarbonylaminonaphthalen-2- --.
Line 19, "1-[(I-Hydroxy-2-acetylaminonaphthalen-5-ylcarbamoyl)" should
read -- 1-[(1-Hydroxy-2-acetylaminonaphthalen-5-ylcarbamoyl) --.
Line 21, "1-[(I-Hydroxy-2-methoxycarbonylaminonaphthalen-5-" should
read -- 1-[(1-Hydroxy-2-methoxycarbonylaminonaphthalen-5- --.
Line 24, "1-[(I-Hydroxy-5-methanesulphonylaminonaphthalen-2-" should read
-- 1-[(1-Hydroxy-5-methanesulphonylaminonaphthalen-2- --.
Line 27, "1-[(I-Hydroxy-8-aminonaphthalen-2-ylcarbamoyl)methyl]" should
read -- 1-[(1-Hydroxy-8-aminonaphthalen-2-ylcarbamoyl)methyl] --.
Line 29, "1-[(I-Hydroxy-8-acetylaminonaphthalen-2-ylcarbamoyl)" should
read -- 1-[(1-Hydroxy-8-acetylaminonaphthalen-2-ylcarbamoyl) --.
Line 31, "1-[(I-Hydroxy-8-methoxycarbonylaminonaphthalen-2-" should
read -- 1-[(1-Hydroxy-8-methoxycarbonylaminonaphthalen-2- --.
Line 34, "1-[(I-Hydroxy-2-acetylaminonaphthalen-8-ylcarbamoyl)" should
read -- 1-[(1-Hydroxy-2-acetylaminonaphthalen-8-ylcarbamoyl) --.
Line 36, "1-[(I-Hydroxy-2-methoxycarbonylaminonaphthalen-8-" should
read -- 1-[(1-Hydroxy-2-methoxycarbonylaminonaphthalen-8- --.
Line 39, "1-[(I-Hydroxy-8-methanesulphonylaminonaphthalen-2-"
should read -- 1-[(1-Hydroxy-8-methanesulphonylaminonaphthalen-2- --.

Column 34,
Lines 26-27, "may unsubstituted" should read -- may be unsubstituted- --.
Lines 65-66, "branch (es)" should read -- branch(es) --.

Column 35,
Line 49, "B an" should read -- B represents an --.

Column 37,
Line 59, "may unsubstituted" should read -- may be unsubstituted --.

UNITED STATES PATENT AND TRADEMARK OFFICE
CERTIFICATE OF CORRECTION

PATENT NO. : 6,605,124 B1
DATED : August 12, 2003
INVENTOR(S) : Jean-Jacques Vandenbossche et al.

It is certified that error appears in the above-identified patent and that said Letters Patent is hereby corrected as shown below:

Column 40,
Line 15, "radicals; q" should read -- radicals; --.

Column 41,
Line 60, "may unsubstituted" should read -- may be unsubstituted --.

Column 45,
Line 46, "may unsubstituted" should read -- may be unsubstituted --.

Signed and Sealed this

Twenty-fourth Day of February, 2004

JON W. DUDAS
*Acting Director of the United States Patent and Trademark Office*